US009447175B2

(12) United States Patent
Pfeil et al.

(10) Patent No.: US 9,447,175 B2
(45) Date of Patent: Sep. 20, 2016

(54) MEANS AND METHODS FOR MANUFACTURING HIGHLY PURE NEUROTOXIN

(75) Inventors: Michael Pfeil, Konigstein (DE); Josef Friedrich, Rauenberg (DE); Harold Victor Taylor, Frankfurt am Main (DE); Karl-Heinz Eisele, Frankfurt am Main (DE); Cornelia Brunn, Frankfurt am Main (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 249 days.

(21) Appl. No.: 13/138,452

(22) PCT Filed: Feb. 17, 2010

(86) PCT No.: PCT/EP2010/000985
§ 371 (c)(1),
(2), (4) Date: Sep. 19, 2011

(87) PCT Pub. No.: WO2010/094463
PCT Pub. Date: Aug. 26, 2010

(65) Prior Publication Data
US 2012/0004179 A1    Jan. 5, 2012

Related U.S. Application Data

(60) Provisional application No. 61/207,989, filed on Feb. 19, 2009, provisional application No. 61/275,173, filed on Aug. 26, 2009.

(30) Foreign Application Priority Data

Feb. 19, 2009    (EP) ..................... 09153226
Aug. 26, 2009    (EP) ..................... 09168679

(51) Int. Cl.
C07K 14/33    (2006.01)
C07K 1/36     (2006.01)
C07K 16/12    (2006.01)
C07K 5/083    (2006.01)
C07K 5/087    (2006.01)
C07K 5/09     (2006.01)
A61K 38/00    (2006.01)

(52) U.S. Cl.
CPC ........... *C07K 16/1282* (2013.01); *C07K 5/081* (2013.01); *C07K 5/0808* (2013.01); *C07K 5/0812* (2013.01); *C07K 5/0815* (2013.01); *A61K 38/00* (2013.01)

(58) Field of Classification Search
None
See application file for complete search history.

(56) References Cited

U.S. PATENT DOCUMENTS

| 5,677,182 A      | 10/1997 | Kriegler      |
| 2006/0177881 A1  | 8/2006  | Bavari et al. |
| 2008/0103098 A1  | 5/2008  | Specht        |
| 2008/0171347 A1  | 7/2008  | Atassi        |
| 2009/0018081 A1  | 1/2009  | Steward       |

FOREIGN PATENT DOCUMENTS

| EP | 2049156         | 4/2009  |
| WO | WO 01/19863     | 3/2001  |
| WO | WO 02/23195     | 3/2002  |
| WO | WO 02/36758     | 3/2002  |
| WO | WO 2005/016232  | 2/2005  |
| WO | WO 2008/157374  | 12/2008 |
| WO | WO 2009/014854  | 1/2009  |

OTHER PUBLICATIONS

Singh et al. Improved Method for Linear B-Cell Epitope Prediction Using Antigen's Primary Sequence. PLoS One. May 7, 2013;8(5):e62216. doi: 10.1371/journal.pone.0062216. Print 2013.*
Lacy et al. Crystal structure of botulinum neurotoxin type A and implications for toxicity. Nat Struct Biol. Oct. 1998;5(10):898-902.*
Antharavally and DasGupta 1997, J Protein Chem 16, 787-799.
Antharavally and DasGupta 1998, J Protein Chem 17, 417-428.
B.R. Dasgupta, et al., Toxicon, vol. 22, No. 3, p. 415-424, Jan. 1, 1984.
Beecher and DasGupta 1997, J Protein Chem 16, 701-712.
C.K. Tse, et al., European Journal of Biochemistry, vol. 122, No. 3, p. 493-500, Mar. 1, 1982.
DasGupta 1984, Toxicon 22, 415-424.
Fischer 2007, PNAS 104, 10447-10452.
International Search Report for PCT/EP2010/000985 of Apr. 19, 2010.
J.A. Chaddock, et al., Protein Expression and Purification, vol. 25, No. 2, p. 219-228, 2002.
Jost 2007, Drugs 67(5), 669-683.
Krieglstein 1990, Eur J Biochem 188, 39-45.
Krieglstein 1994, J Protein Chem 13, 49-57.
Krieglstein, 1991, Eur J Biochem 202, 41-51.

(Continued)

*Primary Examiner* — Gregory S Emch
(74) *Attorney, Agent, or Firm* — Hueschen and Sage

(57) ABSTRACT

The present invention relates to an antibody which specifically binds to unprocessed and/or partially processed neurotoxin polypeptide or an antibody which specifically binds an epitope consisting of a peptide having an amino acid sequence as shown in any one of SEQ ID NOs: 1 to 16 and to methods for the manufacture of such antibodies. Moreover, the present invention relates to a composition comprising processed neurotoxin polypeptide free of unprocessed or partially processed neurotoxin polypeptide and a method for manufacturing said neurotoxin polypeptide based on the antibodies of the invention. The present invention also relates to the use of the aforementioned antibody for separating processed neurotoxin polypeptides from unprocessed or partially processed neurotoxin polypeptides or for determining unprocessed or partially processed neurotoxin polypeptides. The present invention relates to a method for the manufacture of a medicament.

5 Claims, 3 Drawing Sheets

(56) References Cited

OTHER PUBLICATIONS

Figure 3:
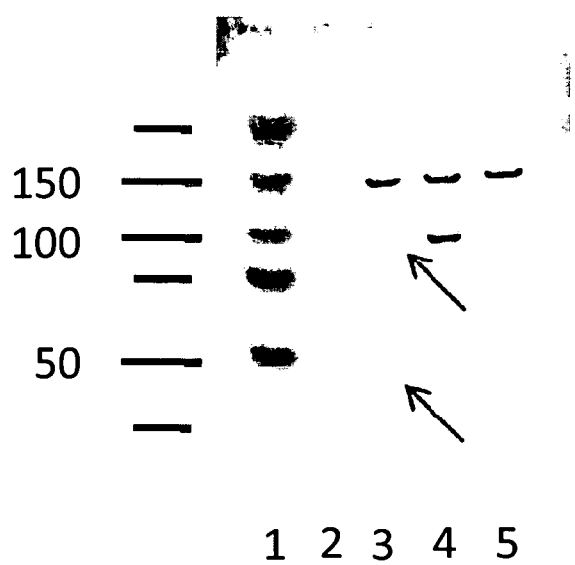

Ogert R.A., et al. Analytical Biochemistry, vol. 205, No. 2, p. 306-312, Sep. 1, 1992.
S. Kalb, et al., Plos One, vol. 4, No. 4, p. E5355-1, Apr. 29, 2009.
Sagane et al. 1999, J Protein Chem 18, 885-892.
Sathyamoorthy 1985, J Biol Chemistry 260, 10461-10466.
V. Sathyamoorthy, et al., Journal of Biological Chemistry, vol. 260, No. 19, p. 10461-10466, Sep. 5, 1985.
Campbell, Biochim Biophys Acta, 1993, vol. 1216, No. 3, p. 487-491.
Couesnon, Microbiology, 2006, vol. 152, p. 759-770.
Dessler, Mov Disorder, 2005, vol. 20, p. 1517-1619.
Ferreira J L, et al., Journal of Food Protection, vol. 67, No. 1, p. 230-206 Abstract, Jan. 1, 2004.
Pearce, Toxicol Appl Pharmacol. 1994, vol. 128, p. 69-77.
Rasooly Reuven, et al., Applied and Environmental Microbiology, vol. 74, No. 14, p. 4309-4313 Abstract, Jul. 1, 2008.
Silberstein, Pain Practice 4, S19-S26, 2004.
Stanker, L.H., et al., Development and partial characterization of high-affinity monoclonal antibodies for botulinum toxin type A and their use in analysis of milk by sandwich ELISA, Journal of Immunological Methods, 336, 2008, 1-8.
Stevens, et al. "Crystallization and Preliminary X-ray Analysis of Botulinum Neurotoxin Type A" J. Mol. Biol. 222:877-880, 1991.
Schantz, et al. "Properties and Use of Botulinum Toxin and other Microbial Neurotoxins in Medicine", Microbiological Reviews, 1992, 56:80-99.

* cited by examiner

Fig. 1

Fig. 2

SEQUENCE LISTING

```
<160> NUMBER OF SEQ ID NOS: 28

<210> SEQ ID NO 1
<211> LENGTH: 10
<212> TYPE: PRT
<213> ORGANISM: Clostridium botulinum

<400> SEQUENCE: 1

Thr Lys Ser Leu Asp Lys Gly Tyr Asn Lys
1               5                   10

<210> SEQ ID NO 2
<211> LENGTH: 10
<212> TYPE: PRT
<213> ORGANISM: Clostridium botulinum

<400> SEQUENCE: 2

Cys Lys Ser Val Lys Ala Pro Gly Ile Cys
1               5                   10

<210> SEQ ID NO 3
<211> LENGTH: 5
<212> TYPE: PRT
<213> ORGANISM: Clostridium botulinum

<400> SEQUENCE: 3

Ser Leu Tyr Asn Lys
1               5

<210> SEQ ID NO 4
<211> LENGTH: 3
<212> TYPE: PRT
<213> ORGANISM: Clostridium botulinum

<400> SEQUENCE: 4

Asn Ser Arg
1

<210> SEQ ID NO 5
<211> LENGTH: 3
<212> TYPE: PRT
<213> ORGANISM: Clostridium botulinum

<400> SEQUENCE: 5

Gly Ile Arg
1

<210> SEQ ID NO 6
<211> LENGTH: 4
<212> TYPE: PRT
<213> ORGANISM: Clostridium botulinum

<400> SEQUENCE: 6

Lys Gly Thr Lys
1

<210> SEQ ID NO 7
<211> LENGTH: 4
```

```
<212> TYPE: PRT
<213> ORGANISM: Clostridium botulinum

<400> SEQUENCE: 7

Asn Gly Thr Lys
1

<210> SEQ ID NO 8
<211> LENGTH: 6
<212> TYPE: PRT
<213> ORGANISM: Clostridium tetani

<400> SEQUENCE: 8

Glu Asn Leu Tyr Asn Arg
1               5

<210> SEQ ID NO 9
<211> LENGTH: 31
<212> TYPE: PRT
<213> ORGANISM: Clostridium botulinum

<400> SEQUENCE: 9

Lys Leu Leu Cys Val Arg Gly Ile Ile Thr Ser Lys Thr Lys Ser Leu
1               5                   10                  15

Asp Lys Gly Tyr Asn Lys Ala Leu Asn Asp Leu Cys Ile Lys Val
            20                  25                  30

<210> SEQ ID NO 10
<211> LENGTH: 16
<212> TYPE: PRT
<213> ORGANISM: Clostridium botulinum

<400> SEQUENCE: 10

Ile Gln Met Cys Lys Ser Val Lys Ala Pro Gly Ile Cys Ile Asp Val
1               5                   10                  15

<210> SEQ ID NO 11
<211> LENGTH: 25
<212> TYPE: PRT
<213> ORGANISM: Clostridium botulinum

<400> SEQUENCE: 11

Thr Lys Phe Cys His Lys Ala Ile Asp Gly Arg Ser Leu Tyr Asn Lys
1               5                   10                  15

Thr Leu Asp Cys Arg Glu Leu Leu Val
            20                  25

<210> SEQ ID NO 12
<211> LENGTH: 20
<212> TYPE: PRT
<213> ORGANISM: Clostridium botulinum

<400> SEQUENCE: 12

Thr Lys Val Cys Leu Arg Leu Thr Lys Asn Ser Arg Asp Asp Ser Thr
1               5                   10                  15

Cys Ile Lys Val
            20

<210> SEQ ID NO 13
<211> LENGTH: 21
<212> TYPE: PRT
<213> ORGANISM: Clostridium botulinum

<400> SEQUENCE: 13
```

```
Ile Arg Phe Cys Lys Asn Ile Val Ser Val Lys Gly Ile Arg Lys Ser
1               5                   10                  15

Ile Cys Ile Glu Ile
            20

<210> SEQ ID NO 14
<211> LENGTH: 23
<212> TYPE: PRT
<213> ORGANISM: Clostridium botulinum

<400> SEQUENCE: 14

Val Lys Phe Cys Lys Ser Val Ile Pro Arg Lys Gly Thr Lys Ala Pro
1               5                   10                  15

Pro Arg Leu Cys Ile Arg Val
            20

<210> SEQ ID NO 15
<211> LENGTH: 21
<212> TYPE: PRT
<213> ORGANISM: Clostridium botulinum

<400> SEQUENCE: 15

Ile Ala Met Cys Lys Pro Val Met Tyr Lys Asn Thr Gly Lys Ser Glu
1               5                   10                  15

Gln Cys Ile Ile Val
            20

<210> SEQ ID NO 16
<211> LENGTH: 35
<212> TYPE: PRT
<213> ORGANISM: Clostridium tetani

<400> SEQUENCE: 16

Ile Gly Leu Cys Lys Lys Ile Ile Pro Pro Thr Asn Ile Arg Glu Asn
1               5                   10                  15

Leu Tyr Asn Arg Thr Ala Ser Leu Thr Asp Leu Gly Gly Glu Leu Cys
                20                  25                  30

Ile Lys Ile
        35

<210> SEQ ID NO 17
<211> LENGTH: 1296
<212> TYPE: PRT
<213> ORGANISM: Clostridium botulinum

<400> SEQUENCE: 17

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
                35                  40                  45

Asp Thr Phe Thr Asn Pro Glu Glu Gly Asp Leu Asn Pro Pro Pro Glu
            50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
```

```
            100                 105                 110
Arg Gly Ile Pro Phe Trp Gly Gly Ser Thr Ile Asp Thr Glu Leu Lys
            115                 120                 125
Val Ile Asp Thr Asn Cys Ile Asn Val Ile Gln Pro Asp Gly Ser Tyr
            130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                    165                 170                 175
Arg Asn Gly Tyr Gly Ser Thr Gln Tyr Ile Arg Phe Ser Pro Asp Phe
                    180                 185                 190
Thr Phe Gly Phe Glu Glu Ser Leu Glu Val Asp Thr Asn Pro Leu Leu
            195                 200                 205
Gly Ala Gly Lys Phe Ala Thr Asp Pro Ala Val Thr Leu Ala His Glu
            210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                    245                 250                 255
Glu Val Ser Phe Glu Glu Leu Arg Thr Phe Gly Gly His Asp Ala Lys
                    260                 265                 270
Phe Ile Asp Ser Leu Gln Glu Asn Glu Phe Arg Leu Tyr Tyr Tyr Asn
                    275                 280                 285
Lys Phe Lys Asp Ile Ala Ser Thr Leu Asn Lys Ala Lys Ser Ile Val
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                    325                 330                 335
Lys Phe Asp Lys Leu Tyr Lys Met Leu Thr Glu Ile Tyr Thr Glu Asp
                    340                 345                 350
Asn Phe Val Lys Phe Phe Lys Val Leu Asn Arg Lys Thr Tyr Leu Asn
                    355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                    405                 410                 415
Lys Asn Phe Thr Gly Leu Phe Glu Phe Tyr Lys Leu Leu Cys Val Arg
                    420                 425                 430
Gly Ile Ile Thr Ser Lys Thr Lys Ser Leu Asp Lys Gly Tyr Asn Lys
                    435                 440                 445
Ala Leu Asn Asp Leu Cys Ile Lys Val Asn Asn Trp Asp Leu Phe Phe
            450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                    485                 490                 495
Asp Leu Ile Gln Gln Tyr Tyr Leu Thr Phe Asn Phe Asp Asn Glu Pro
                    500                 505                 510
Glu Asn Ile Ser Ile Glu Asn Leu Ser Ser Asp Ile Ile Gly Gln Leu
                    515                 520                 525
```

```
Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Phe Val Gly Ala Leu
            645                 650                 655

Ile Phe Ser Gly Ala Val Ile Leu Leu Glu Phe Ile Pro Glu Ile Ala
        660                 665                 670

Ile Pro Val Leu Gly Thr Phe Ala Leu Val Ser Tyr Ile Ala Asn Lys
    675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
930                 935                 940
```

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
1010                1015                1020

Leu Asn Asn Ser Lys Ile Tyr Ile Asn Gly Arg Leu Ile Asp Gln
1025                1030                1035

Lys Pro Ile Ser Asn Leu Gly Asn Ile His Ala Ser Asn Asn Ile
1040                1045                1050

Met Phe Lys Leu Asp Gly Cys Arg Asp Thr His Arg Tyr Ile Trp
1055                1060                1065

Ile Lys Tyr Phe Asn Leu Phe Asp Lys Glu Leu Asn Glu Lys Glu
1070                1075                1080

Ile Lys Asp Leu Tyr Asp Asn Gln Ser Asn Ser Gly Ile Leu Lys
1085                1090                1095

Asp Phe Trp Gly Asp Tyr Leu Gln Tyr Asp Lys Pro Tyr Tyr Met
1100                1105                1110

Leu Asn Leu Tyr Asp Pro Asn Lys Tyr Val Asp Val Asn Asn Val
1115                1120                1125

Gly Ile Arg Gly Tyr Met Tyr Leu Lys Gly Pro Arg Gly Ser Val
1130                1135                1140

Met Thr Thr Asn Ile Tyr Leu Asn Ser Ser Leu Tyr Arg Gly Thr
1145                1150                1155

Lys Phe Ile Ile Lys Lys Tyr Ala Ser Gly Asn Lys Asp Asn Ile
1160                1165                1170

Val Arg Asn Asn Asp Arg Val Tyr Ile Asn Val Val Val Lys Asn
1175                1180                1185

Lys Glu Tyr Arg Leu Ala Thr Asn Ala Ser Gln Ala Gly Val Glu
1190                1195                1200

Lys Ile Leu Ser Ala Leu Glu Ile Pro Asp Val Gly Asn Leu Ser
1205                1210                1215

Gln Val Val Val Met Lys Ser Lys Asn Asp Gln Gly Ile Thr Asn
1220                1225                1230

Lys Cys Lys Met Asn Leu Gln Asp Asn Asn Gly Asn Asp Ile Gly
1235                1240                1245

Phe Ile Gly Phe His Gln Phe Asn Asn Ile Ala Lys Leu Val Ala
1250                1255                1260

Ser Asn Trp Tyr Asn Arg Gln Ile Glu Arg Ser Arg Thr Leu
1265                1270                1275

Gly Cys Ser Trp Glu Phe Ile Pro Val Asp Asp Gly Trp Gly Glu
1280                1285                1290

Arg Pro Leu
1295

<210> SEQ ID NO 18
<211> LENGTH: 1291
<212> TYPE: PRT
<213> ORGANISM: Clostridium botulinum

<400> SEQUENCE: 18

-continued

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
                180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
    275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
    340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415
```

```
Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
```

```
              835                 840                 845
Leu Ile Glu Met Phe Asn Lys Tyr Asn Ser Glu Ile Leu Asn Asn Ile
          850                 855                 860

Ile Leu Asn Leu Arg Tyr Lys Asp Asn Leu Ile Asp Leu Ser Gly
865                 870                 875                 880

Tyr Gly Ala Lys Val Glu Val Tyr Asp Gly Val Glu Leu Asn Asp Lys
                      885                 890                 895

Asn Gln Phe Lys Leu Thr Ser Ser Ala Asn Ser Lys Ile Arg Val Thr
              900                 905                 910

Gln Asn Gln Asn Ile Ile Phe Asn Ser Val Phe Leu Asp Phe Ser Val
              915                 920                 925

Ser Phe Trp Ile Arg Ile Pro Lys Tyr Lys Asn Asp Gly Ile Gln Asn
          930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                      965                 970                 975

Asp Ile Asn Gly Lys Thr Lys Ser Val Phe Phe Glu Tyr Asn Ile Arg
                  980                 985                 990

Glu Asp Ile Ser Glu Tyr Ile Asn  Arg Trp Phe Phe Val  Thr Ile Thr
                  995                 1000                1005

Asn Asn  Leu Asn Asn Ala Lys  Ile Tyr Ile Asn Gly  Lys Leu Glu
    1010                1015                 1020

Ser Asn  Thr Asp Ile Lys Asp  Ile Arg Glu Val Ile  Ala Asn Gly
    1025                1030                 1035

Glu Ile  Ile Phe Lys Leu Asp  Gly Asp Ile Asp Arg  Thr Gln Phe
    1040                1045                 1050

Ile Trp  Met Lys Tyr Phe Ser  Ile Phe Asn Thr Glu  Leu Ser Gln
    1055                1060                 1065

Ser Asn  Ile Glu Glu Arg Tyr  Lys Ile Gln Ser Tyr  Ser Glu Tyr
    1070                1075                 1080

Leu Lys  Asp Phe Trp Gly Asn  Pro Leu Met Tyr Asn  Lys Glu Tyr
    1085                1090                 1095

Tyr Met  Phe Asn Ala Gly Asn  Lys Asn Ser Tyr Ile  Lys Leu Lys
    1100                1105                 1110

Lys Asp  Ser Pro Val Gly Glu  Ile Leu Thr Arg Ser  Lys Tyr Asn
    1115                1120                 1125

Gln Asn  Ser Lys Tyr Ile Asn  Tyr Arg Asp Leu Tyr  Ile Gly Glu
    1130                1135                 1140

Lys Phe  Ile Ile Arg Arg Lys  Ser Asn Ser Gln Ser  Ile Asn Asp
    1145                1150                 1155

Asp Ile  Val Arg Lys Glu Asp  Tyr Ile Tyr Leu Asp  Phe Phe Asn
    1160                1165                 1170

Leu Asn  Gln Glu Trp Arg Val  Tyr Thr Tyr Lys Tyr  Phe Lys Lys
    1175                1180                 1185

Glu Glu  Glu Lys Leu Phe Leu  Ala Pro Ile Ser Asp  Ser Asp Glu
    1190                1195                 1200

Phe Tyr  Asn Thr Ile Gln Ile  Lys Glu Tyr Asp Glu  Gln Pro Thr
    1205                1210                 1215

Tyr Ser  Cys Gln Leu Leu Phe  Lys Lys Asp Glu Glu  Ser Thr Asp
    1220                1225                 1230

Glu Ile  Gly Leu Ile Gly Ile  His Arg Phe Tyr Glu  Ser Gly Ile
    1235                1240                 1245
```

```
Val Phe Glu Glu Tyr Lys Asp Tyr Phe Cys Ile Ser Lys Trp Tyr
    1250            1255                1260

Leu Lys Glu Val Lys Arg Lys Pro Tyr Asn Leu Lys Leu Gly Cys
    1265            1270                1275

Asn Trp Gln Phe Ile Pro Lys Asp Glu Gly Trp Thr Glu
    1280            1285                1290

<210> SEQ ID NO 19
<211> LENGTH: 1280
<212> TYPE: PRT
<213> ORGANISM: Clostridium botulinum

<400> SEQUENCE: 19

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Ile Gly Asn Ile Trp Val Ile Pro Asp
        35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asn
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Arg Ile Ser Ser Val Thr Ser Asn Ile
                245                 250                 255

Phe Tyr Ser Gln Tyr Lys Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
```

```
                325                 330                 335
Ser Gly Glu Val Ala Val Asp Arg Asn Lys Phe Ala Glu Leu Tyr Lys
            340                 345                 350
Glu Leu Thr Gln Ile Phe Thr Glu Phe Asn Tyr Ala Lys Ile Tyr Asn
            355                 360                 365
Val Gln Asn Arg Lys Ile Tyr Leu Ser Asn Val Tyr Thr Pro Val Thr
            370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
            405                 410                 415
Arg Asn Pro Ala Leu Arg Lys Val Asn Pro Glu Asn Met Leu Tyr Leu
            420                 425                 430
Phe Thr Lys Phe Cys His Lys Ala Ile Asp Gly Arg Ser Leu Tyr Asn
            435                 440                 445
Lys Thr Leu Asp Cys Arg Glu Leu Leu Val Lys Asn Thr Asp Leu Pro
            450                 455                 460
Phe Ile Gly Asp Ile Ser Asp Ile Lys Thr Asp Ile Phe Leu Ser Lys
465                 470                 475                 480
Asp Ile Asn Glu Glu Thr Glu Val Ile Asp Tyr Pro Asp Asn Val Ser
            485                 490                 495
Val Asp Gln Val Ile Leu Ser Lys Asn Thr Ser Glu His Gly Gln Leu
            500                 505                 510
Asp Leu Leu Tyr Pro Ile Ile Glu Gly Glu Ser Gln Val Leu Pro Gly
            515                 520                 525
Glu Asn Gln Val Phe Tyr Asp Asn Arg Thr Gln Asn Val Asp Tyr Leu
            530                 535                 540
Asn Ser Tyr Tyr Tyr Leu Glu Ser Gln Lys Leu Ser Asp Asn Val Glu
545                 550                 555                 560
Asp Phe Thr Phe Thr Thr Ser Ile Glu Glu Ala Leu Asp Asn Ser Gly
            565                 570                 575
Lys Val Tyr Thr Tyr Phe Pro Lys Leu Ala Asp Lys Val Asn Thr Gly
            580                 585                 590
Val Gln Gly Gly Leu Phe Leu Met Trp Ala Asn Asp Val Val Glu Asp
            595                 600                 605
Phe Thr Thr Asn Ile Leu Arg Lys Asp Thr Leu Asp Lys Ile Ser Asp
            610                 615                 620
Val Ser Ala Ile Ile Pro Tyr Ile Gly Pro Ala Leu Asn Ile Ser Asn
625                 630                 635                 640
Ser Val Arg Arg Gly Asn Phe Thr Glu Ala Phe Ala Val Thr Gly Val
            645                 650                 655
Thr Ile Leu Leu Glu Ala Phe Gln Glu Phe Thr Ile Pro Ala Leu Gly
            660                 665                 670
Ala Phe Val Ile Tyr Ser Lys Val Gln Glu Arg Asn Glu Ile Ile Lys
            675                 680                 685
Thr Ile Asp Asn Cys Leu Glu Gln Arg Ile Lys Arg Trp Lys Asp Ser
            690                 695                 700
Tyr Glu Trp Met Ile Gly Thr Trp Leu Ser Arg Ile Thr Thr Gln Phe
705                 710                 715                 720
Asn Asn Ile Ser Tyr Gln Met Tyr Asp Ser Leu Asn Tyr Gln Ala Asp
            725                 730                 735
Ala Ile Lys Asp Lys Ile Asp Leu Glu Tyr Lys Lys Tyr Ser Gly Ser
            740                 745                 750
```

-continued

Asp Lys Glu Asn Ile Lys Ser Gln Val Glu Asn Leu Lys Asn Ser Leu
        755                 760                 765

Asp Ile Lys Ile Ser Glu Ala Met Asn Asn Ile Asn Lys Phe Ile Arg
770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
            805                 810                 815

Leu Ile Asp Ser His Asn Ile Ile Leu Val Gly Glu Val Asp Arg Leu
        820                 825                 830

Lys Ala Lys Val Asn Glu Ser Phe Glu Asn Thr Ile Pro Phe Asn Ile
            835                 840                 845

Phe Ser Tyr Thr Asn Asn Ser Leu Leu Lys Asp Ile Ile Asn Glu Tyr
    850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
            900                 905                 910

Ser Ser Gly Asp Lys Ile Ile Val Asn Leu Asn Asn Ile Leu Tyr
        915                 920                 925

Ser Ala Ile Tyr Glu Asn Ser Ser Val Ser Phe Trp Ile Lys Ile Ser
    930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
            980                 985                 990

Tyr Ser Glu Ser Leu Ser His Thr Gly Tyr Thr Asn Lys Trp Phe Phe
        995                 1000                1005

Val Thr Ile Thr Asn Asn Ile Met Gly Tyr Met Lys Leu Tyr Ile
    1010                1015                1020

Asn Gly Glu Leu Lys Gln Ser Glu Arg Ile Glu Asp Leu Asn Glu
    1025                1030                1035

Val Lys Leu Asp Lys Thr Ile Val Phe Gly Ile Asp Glu Asn Ile
    1040                1045                1050

Asp Glu Asn Gln Met Leu Trp Ile Arg Asp Phe Asn Ile Phe Ser
    1055                1060                1065

Lys Glu Leu Ser Asn Glu Asp Ile Asn Ile Val Tyr Glu Gly Gln
    1070                1075                1080

Ile Leu Arg Asn Val Ile Lys Asp Tyr Trp Gly Asn Pro Leu Lys
    1085                1090                1095

Phe Asp Thr Glu Tyr Tyr Ile Ile Asn Asp Asn Tyr Ile Asp Arg
    1100                1105                1110

Tyr Ile Ala Pro Lys Ser Asn Ile Leu Val Leu Val Gln Tyr Pro
    1115                1120                1125

Asp Arg Ser Lys Leu Tyr Thr Gly Asn Pro Ile Thr Ile Lys Ser
    1130                1135                1140

Val Ser Asp Lys Asn Pro Tyr Ser Arg Ile Leu Asn Gly Asp Asn
    1145                1150                1155

```
Ile Met Phe His Met Leu Tyr Asn Ser Gly Lys Tyr Met Ile Ile
    1160                1165                1170

Arg Asp Thr Asp Thr Ile Tyr Ala Ile Glu Gly Arg Glu Cys Ser
    1175                1180                1185

Lys Asn Cys Val Tyr Ala Leu Lys Leu Gln Ser Asn Leu Gly Asn
    1190                1195                1200

Tyr Gly Ile Gly Ile Phe Ser Ile Lys Asn Ile Val Ser Gln Asn
    1205                1210                1215

Lys Tyr Cys Ser Gln Ile Phe Ser Ser Phe Met Lys Asn Thr Met
    1220                1225                1230

Leu Leu Ala Asp Ile Tyr Lys Pro Trp Arg Phe Ser Phe Glu Asn
    1235                1240                1245

Ala Tyr Thr Pro Val Ala Val Thr Asn Tyr Glu Thr Lys Leu Leu
    1250                1255                1260

Ser Thr Ser Ser Phe Trp Lys Phe Ile Ser Arg Asp Pro Gly Trp
    1265                1270                1275

Val Glu
    1280

<210> SEQ ID NO 20
<211> LENGTH: 1285
<212> TYPE: PRT
<213> ORGANISM: Clostridium botulinum

<400> SEQUENCE: 20

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
                100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
                180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240
```

-continued

```
Ile Asn Ile Pro Ser Asp Lys Arg Ile Arg Pro Gln Val Ser Glu Gly
            245                 250                 255

Phe Phe Ser Gln Asp Gly Pro Asn Val Gln Phe Glu Glu Leu Tyr Thr
            260                 265                 270

Phe Gly Gly Ser Asp Val Glu Ile Ile Pro Gln Ile Glu Arg Leu Gln
            275                 280                 285

Leu Arg Glu Lys Ala Leu Gly His Tyr Lys Asp Ile Ala Lys Arg Leu
            290                 295                 300

Asn Asn Ile Asn Lys Thr Ile Pro Ser Ser Trp Ser Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
                340                 345                 350

Asp Leu Thr Asn Val Met Ser Glu Val Val Tyr Ser Ser Gln Tyr Asn
            355                 360                 365

Val Lys Asn Arg Thr His Tyr Phe Ser Lys His Tyr Leu Pro Val Phe
            370                 375                 380

Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
                420                 425                 430

Phe Thr Lys Val Cys Leu Arg Leu Thr Arg Asn Ser Arg Asp Asp Ser
            435                 440                 445

Thr Cys Ile Gln Val Lys Asn Asn Thr Leu Pro Tyr Val Ala Asp Lys
            450                 455                 460

Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Glu Ser Ile
                485                 490                 495

Leu Asp Ala Lys Val Pro Thr Asn Pro Glu Ala Val Asp Pro Leu Leu
            500                 505                 510

Pro Asn Val Asn Met Glu Pro Leu Asn Val Pro Gly Glu Glu Glu Val
            515                 520                 525

Phe Tyr Asp Asp Ile Thr Lys Asp Val Asp Tyr Leu Asn Ser Tyr Tyr
            530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
                580                 585                 590

Leu Phe Leu Asn Trp Ala Asn Glu Val Val Glu Asp Phe Thr Thr Asn
            595                 600                 605

Ile Met Lys Lys Asp Thr Leu Asp Lys Ile Ser Asp Val Ser Ala Ile
610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655
```

```
Glu Gly Phe Pro Glu Phe Thr Ile Pro Ala Leu Gly Val Phe Thr Phe
                660                 665                 670

Tyr Ser Ser Ile Gln Glu Arg Glu Lys Ile Ile Lys Thr Ile Glu Asn
            675                 680                 685

Cys Leu Glu Gln Arg Val Lys Arg Trp Lys Asp Ser Tyr Gln Trp Met
        690                 695                 700

Val Ser Asn Trp Leu Ser Arg Ile Thr Thr Arg Phe Asn His Ile Ser
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
    770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Ile Pro Phe Asn Ile Phe Ser Tyr Thr
        835                 840                 845

Asn Asn Ser Leu Leu Lys Asp Met Ile Asn Glu Tyr Phe Asn Ser Ile
    850                 855                 860

Asn Asp Ser Lys Ile Leu Ser Leu Gln Asn Lys Lys Asn Thr Leu Met
865                 870                 875                 880

Asp Thr Ser Gly Tyr Asn Ala Glu Val Arg Val Glu Gly Asn Val Gln
                885                 890                 895

Leu Asn Pro Ile Phe Pro Phe Asp Phe Lys Leu Gly Ser Ser Gly Asp
            900                 905                 910

Asp Arg Gly Lys Val Ile Val Thr Gln Asn Glu Asn Ile Val Tyr Asn
        915                 920                 925

Ala Met Tyr Glu Ser Phe Ser Ile Ser Phe Trp Ile Arg Ile Asn Lys
    930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                965                 970                 975

Leu Lys Gln Asn Glu Asn Ser Glu Gln Asp Ile Asn Phe Ser Tyr Asp
            980                 985                 990

Ile Ser Lys Asn Ala Ala Gly Tyr Asn Lys Trp Phe Phe Val Thr Ile
        995                 1000                1005

Thr Thr Asn Met Met Gly Asn Met Met Ile Tyr Ile Asn Gly Lys
    1010                1015                1020

Leu Ile Asp Thr Ile Lys Val Lys Glu Leu Thr Gly Ile Asn Phe
    1025                1030                1035

Ser Lys Thr Ile Thr Phe Gln Met Asn Lys Ile Pro Asn Thr Gly
    1040                1045                1050

Leu Ile Thr Ser Asp Ser Asp Asn Ile Asn Met Trp Ile Arg Asp
    1055                1060                1065

Phe Tyr Ile Phe Ala Lys Glu Leu Asp Asp Lys Asp Ile Asn Ile
```

```
            1070                1075                1080

Leu Phe Asn Ser Leu Gln Tyr Thr Asn Val Val Lys Asp Tyr Trp
       1085                1090                1095

Gly Asn Asp Leu Arg Tyr Asp Lys Glu Tyr Tyr Met Ile Asn Val
   1100                1105                1110

Asn Tyr Met Asn Arg Tyr Met Ser Lys Lys Gly Asn Gly Ile Val
   1115                1120                1125

Phe Asn Thr Arg Lys Asn Asn Asp Phe Asn Glu Gly Tyr Lys
   1130                1135                1140

Ile Ile Ile Lys Arg Ile Arg Gly Asn Thr Asn Asp Thr Arg Val
   1145                1150                1155

Arg Gly Glu Asn Val Leu Tyr Phe Asn Thr Thr Ile Asp Asn Lys
   1160                1165                1170

Gln Tyr Ser Leu Gly Met Tyr Lys Pro Ser Arg Asn Leu Gly Thr
   1175                1180                1185

Asp Leu Val Pro Leu Gly Ala Leu Asp Gln Pro Met Asp Glu Ile
   1190                1195                1200

Arg Lys Tyr Gly Ser Phe Ile Ile Gln Pro Cys Asn Thr Phe Asp
   1205                1210                1215

Tyr Tyr Ala Ser Gln Leu Phe Leu Ser Ser Asn Ala Thr Thr Asn
   1220                1225                1230

Arg Leu Gly Ile Leu Ser Ile Gly Ser Tyr Ser Phe Lys Leu Gly
   1235                1240                1245

Asp Asp Tyr Trp Phe Asn His Glu Tyr Leu Ile Pro Val Ile Lys
   1250                1255                1260

Ile Glu His Tyr Ala Ser Leu Leu Glu Ser Thr Ser Thr His Trp
   1265                1270                1275

Val Phe Val Pro Ala Ser Glu
   1280                1285

<210> SEQ ID NO 21
<211> LENGTH: 1251
<212> TYPE: PRT
<213> ORGANISM: Clostridium botulinum

<400> SEQUENCE: 21

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140
```

-continued

Leu Pro Asn Val Ile Ile Met Gly Ala Glu Pro Asp Leu Phe Glu Thr
145                 150                 155                 160

Asn Ser Ser Asn Ile Ser Leu Arg Asn Tyr Met Pro Ser Asn His
            165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
            195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Arg Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile

-continued

```
                565                 570                 575
Gln Gln Val Leu Val Asp Phe Thr Thr Glu Ala Asn Gln Lys Ser Thr
                580                 585                 590
Val Asp Lys Ile Ala Asp Ile Ser Ile Val Val Pro Tyr Ile Gly Leu
            595                 600                 605
Ala Leu Asn Ile Gly Asn Glu Ala Gln Lys Gly Asn Phe Lys Asp Ala
        610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
            660                 665                 670
Glu Arg Asp Glu Lys Trp Lys Glu Val Tyr Ser Phe Ile Val Ser Asn
        675                 680                 685
Trp Met Thr Lys Ile Asn Thr Gln Phe Asn Lys Arg Lys Glu Gln Met
        690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
                725                 730                 735
Lys Tyr Asp Ile Lys Gln Ile Glu Asn Glu Leu Asn Gln Lys Val Ser
            740                 745                 750
Ile Ala Met Asn Asn Ile Asp Arg Phe Leu Thr Glu Ser Ser Ile Ser
        755                 760                 765
Tyr Leu Met Lys Ile Ile Asn Glu Val Lys Ile Asn Lys Leu Arg Glu
        770                 775                 780
Tyr Asp Glu Asn Val Lys Thr Tyr Leu Leu Asn Tyr Ile Ile Gln His
785                 790                 795                 800
Gly Ser Ile Leu Gly Glu Ser Gln Gln Glu Leu Asn Ser Met Val Thr
                805                 810                 815
Asp Thr Leu Asn Asn Ser Ile Pro Phe Lys Leu Ser Ser Tyr Thr Asp
            820                 825                 830
Asp Lys Ile Leu Ile Ser Tyr Phe Asn Lys Phe Phe Lys Arg Ile Lys
        835                 840                 845
Ser Ser Ser Val Leu Asn Met Arg Tyr Lys Asn Asp Lys Tyr Val Asp
        850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                885                 890                 895
Glu Val Asn Ile Ser Gln Asn Asp Tyr Ile Ile Tyr Asp Asn Lys Tyr
            900                 905                 910
Lys Asn Phe Ser Ile Ser Phe Trp Val Arg Ile Pro Asn Tyr Asp Asn
        915                 920                 925
Lys Ile Val Asn Val Asn Asn Glu Tyr Thr Ile Ile Asn Cys Met Arg
        930                 935                 940
Asp Asn Asn Ser Gly Trp Lys Val Ser Leu Asn His Asn Glu Ile Ile
945                 950                 955                 960
Trp Thr Phe Glu Asp Asn Arg Gly Ile Asn Gln Lys Leu Ala Phe Asn
                965                 970                 975
Tyr Gly Asn Ala Asn Gly Ile Ser Asp Tyr Ile Asn Lys Trp Ile Phe
            980                 985                 990
```

Val Thr Ile Thr Asn Asp Arg Leu Gly Asp Ser Lys Leu Tyr Ile Asn
    995                 1000                1005

Gly Asn Leu Ile Asp Gln Lys Ser Ile Leu Asn Leu Gly Asn Ile
    1010                1015                1020

His Val Ser Asp Asn Ile Leu Phe Lys Ile Val Asn Cys Ser Tyr
    1025                1030                1035

Thr Arg Tyr Ile Gly Ile Arg Tyr Phe Asn Ile Phe Asp Lys Glu
    1040                1045                1050

Leu Asp Glu Thr Glu Ile Gln Thr Leu Tyr Ser Asn Glu Pro Asn
    1055                1060                1065

Thr Asn Ile Leu Lys Asp Phe Trp Gly Asn Tyr Leu Leu Tyr Asp
    1070                1075                1080

Lys Glu Tyr Tyr Leu Leu Asn Val Leu Lys Pro Asn Asn Phe Ile
    1085                1090                1095

Asp Arg Arg Lys Asp Ser Thr Leu Ser Ile Asn Asn Ile Arg Ser
    1100                1105                1110

Thr Ile Leu Leu Ala Asn Arg Leu Tyr Ser Gly Ile Lys Val Lys
    1115                1120                1125

Ile Gln Arg Val Asn Asn Ser Ser Thr Asn Asp Asn Leu Val Arg
    1130                1135                1140

Lys Asn Asp Gln Val Tyr Ile Asn Phe Val Ala Ser Lys Thr His
    1145                1150                1155

Leu Phe Pro Leu Tyr Ala Asp Thr Ala Thr Thr Asn Lys Glu Lys
    1160                1165                1170

Thr Ile Lys Ile Ser Ser Ser Gly Asn Arg Phe Asn Gln Val Val
    1175                1180                1185

Val Met Asn Ser Val Gly Asn Cys Thr Met Asn Phe Lys Asn Asn
    1190                1195                1200

Asn Gly Asn Asn Ile Gly Leu Leu Gly Phe Lys Ala Asp Thr Val
    1205                1210                1215

Val Ala Ser Thr Trp Tyr Tyr Thr His Met Arg Asp His Thr Asn
    1220                1225                1230

Ser Asn Gly Cys Phe Trp Asn Phe Ile Ser Glu Glu His Gly Trp
    1235                1240                1245

Gln Glu Lys
    1250

<210> SEQ ID NO 22
<211> LENGTH: 1280
<212> TYPE: PRT
<213> ORGANISM: Clostridium botulinum

<400> SEQUENCE: 22

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
            20                  25                  30

Tyr Tyr Lys Ala Phe Glu Ile Met Pro Asn Val Trp Ile Met Pro Glu
        35                  40                  45

Arg Asp Thr Ile Gly Thr Lys Pro Asp Glu Phe Gln Val Pro Asp Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn

```
                    85              90                  95
Arg Ile Asn Ser Asn Pro Thr Gly Lys Val Leu Leu Glu Glu Val Ser
                100             105                 110

Asn Ala Arg Pro Tyr Leu Gly Asp Asp Thr Leu Ile Asn Glu Phe
            115             120                 125

Leu Pro Val Asn Val Thr Thr Ser Val Asn Ile Lys Phe Ser Thr Asp
130                     135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165             170                 175

Asp Lys Leu Ile Glu Pro Ser Asn His Gly Phe Gly Ser Ile Asn Ile
            180             185                 190

Leu Thr Phe Ser Pro Glu Tyr Glu His Ile Phe Asn Asp Ile Ser Gly
            195             200                 205

Gly Asn His Asn Ser Thr Glu Ser Phe Ile Ala Asp Pro Ala Ile Ser
210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245             250                 255

Ile Ala Glu Lys Pro Ile Arg Leu Glu Glu Phe Leu Thr Phe Gly Gly
            260             265                 270

Glu Asp Leu Asn Ile Ile Pro Ser Ala Met Lys Glu Lys Ile Tyr Asn
            275             280                 285

Asp Leu Leu Ala Asn Tyr Glu Lys Ile Ala Thr Arg Leu Arg Glu Val
            290             295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325             330                 335

Asn Arg Asn Lys Phe Asn Glu Ile Tyr Lys Lys Leu Tyr Ser Phe Thr
            340             345                 350

Glu Ile Asp Leu Ala Asn Lys Phe Lys Val Lys Cys Arg Asn Thr Tyr
            355             360                 365

Phe Ile Lys Tyr Gly Phe Val Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405             410                 415

Pro Asp Lys Gly Leu Val Glu Lys Ile Ile Lys Phe Cys Lys Ser Ile
            420             425                 430

Ile Pro Arg Lys Gly Thr Lys Gln Ser Pro Ser Leu Cys Ile Arg Val
            435             440                 445

Asn Asn Arg Glu Leu Phe Phe Val Ala Ser Glu Ser Ser Tyr Asn Glu
            450             455                 460

Ser Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485             490                 495

Glu Thr Ile Pro Gln Ile Ser Asn Arg Thr Leu Asn Thr Leu Val Gln
            500             505                 510
```

```
Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
                565                 570                 575

Glu Phe Ile Asp Thr Ile Asn Lys Pro Val Asn Ala Ala Leu Phe Ile
            580                 585                 590

Asp Trp Ile Ser Lys Val Ile Arg Asp Phe Thr Thr Glu Ala Thr Gln
            595                 600                 605

Lys Ser Thr Val Asp Lys Ile Ala Asp Ile Ser Leu Ile Val Pro Tyr
        610                 615                 620

Val Gly Leu Ala Leu Asn Ile Val Ile Glu Ala Glu Lys Gly Asn Phe
625                 630                 635                 640

Glu Glu Ala Phe Glu Leu Leu Gly Ala Gly Ile Leu Leu Glu Phe Val
                645                 650                 655

Pro Glu Leu Thr Ile Pro Val Ile Leu Val Phe Thr Ile Lys Ser Tyr
            660                 665                 670

Ile Asp Ser Tyr Glu Asn Lys Asn Lys Ala Ile Lys Ala Ile Asn Asn
            675                 680                 685

Ser Leu Ile Glu Arg Glu Ala Lys Trp Lys Glu Ile Tyr Ser Trp Ile
        690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Ala Ile Glu Tyr Lys Tyr Asn Asn Tyr Thr Ser Asp Glu Lys Asn Arg
            740                 745                 750

Leu Glu Ser Lys Tyr Asn Ile Asn Asn Ile Glu Glu Glu Leu Asn Lys
        755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Glu Val Gly Lys
785                 790                 795                 800

Leu Lys Glu Tyr Asp Lys His Val Lys Ser Asp Leu Leu Asp Tyr Ile
                805                 810                 815

Leu Tyr His Lys Leu Ile Leu Gly Glu Gln Thr Lys Glu Leu Ile Asp
            820                 825                 830

Leu Val Thr Ser Thr Leu Asn Ser Ser Ile Pro Phe Glu Leu Ser Ser
            835                 840                 845

Tyr Thr Asn Asp Lys Ile Leu Ile Ile Tyr Phe Asn Arg Leu Tyr Lys
850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
                885                 890                 895

Val Tyr Ile Tyr Ser Thr Asn Arg Asn Gln Phe Gly Ile Tyr Ser Gly
            900                 905                 910

Arg Leu Ser Glu Val Asn Ile Ala Gln Asn Asn Asp Ile Ile Tyr Asn
        915                 920                 925
```

```
Ser Arg Tyr Gln Asn Phe Ser Ile Ser Phe Trp Val Thr Ile Pro Lys
930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
            980                 985                 990

Lys Leu Ile Phe Arg Tyr Glu Glu Leu Ala Ser Ile Ser Asp Tyr Ile
        995                 1000                1005

Asn Lys Trp Ile Phe Val Thr Ile Thr Asn Asn Arg Leu Gly Asn
    1010                1015                1020

Ser Arg Ile Tyr Ile Asn Gly Asn Leu Ile Val Glu Lys Ser Ile
    1025                1030                1035

Ser Asn Leu Gly Asp Ile His Val Ser Asp Asn Ile Leu Phe Lys
    1040                1045                1050

Ile Val Gly Cys Asp Asp Glu Thr Tyr Val Gly Ile Arg Tyr Phe
    1055                1060                1065

Lys Val Phe Asn Thr Glu Leu Asp Lys Thr Glu Ile Glu Thr Leu
    1070                1075                1080

Tyr Ser Asn Glu Pro Asp Pro Ser Ile Leu Lys Asp Tyr Trp Gly
    1085                1090                1095

Asn Tyr Leu Leu Tyr Asn Lys Lys Tyr Tyr Leu Phe Asn Leu Leu
    1100                1105                1110

Arg Lys Asp Lys Tyr Ile Thr Arg Asn Ser Gly Ile Leu Asn Ile
    1115                1120                1125

Asn Gln Gln Arg Gly Val Thr Gly Gly Ile Ser Val Phe Leu Asn
    1130                1135                1140

Tyr Lys Leu Tyr Glu Gly Val Glu Val Ile Ile Arg Lys Asn Ala
    1145                1150                1155

Pro Ile Asp Ile Ser Asn Thr Asp Asn Phe Val Arg Lys Asn Asp
    1160                1165                1170

Leu Ala Tyr Ile Asn Val Val Asp His Gly Val Glu Tyr Arg Leu
    1175                1180                1185

Tyr Ala Asp Ile Ser Ile Thr Lys Ser Glu Lys Ile Ile Lys Leu
    1190                1195                1200

Ile Arg Thr Ser Asn Pro Asn Asp Ser Leu Gly Gln Ile Ile Val
    1205                1210                1215

Met Asp Ser Ile Gly Asn Asn Cys Thr Met Asn Phe Gln Asn Asn
    1220                1225                1230

Asp Gly Ser Asn Ile Gly Leu Leu Gly Phe His Ser Asp Asp Leu
    1235                1240                1245

Val Ala Ser Ser Trp Tyr Tyr Asn His Ile Arg Arg Asn Thr Ser
    1250                1255                1260

Ser Asn Gly Cys Phe Trp Ser Phe Ile Ser Lys Glu His Gly Trp
    1265                1270                1275

Lys Glu
1280

<210> SEQ ID NO 23
<211> LENGTH: 1297
<212> TYPE: PRT
<213> ORGANISM: Clostridium botulinum
<220> FEATURE:
<221> NAME/KEY: misc_feature
```

<222> LOCATION: (7)..(7)
<223> OTHER INFORMATION: Xaa can be any naturally occurring amino acid

<400> SEQUENCE: 23

```
Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400
```

-continued

```
Ser Lys Asn Leu Lys Thr Glu Phe Asn Gly Gln Asn Lys Ala Val Asn
            405                 410                 415
Lys Glu Ala Tyr Glu Ile Ser Leu Glu His Leu Val Ile Tyr Arg
        420                 425                 430
Ile Ala Met Cys Lys Pro Val Met Tyr Lys Asn Thr Gly Lys Ser Glu
            435                 440                 445
Gln Cys Ile Ile Val Asn Asn Glu Asp Leu Phe Phe Ile Ala Asn Lys
        450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
            485                 490                 495
Leu Asp Asn Asp Leu Ser Ser Gly Ile Asp Leu Pro Asn Glu Asn Thr
            500                 505                 510
Glu Pro Phe Thr Asn Phe Asp Asp Ile Asp Ile Pro Val Tyr Ile Lys
            515                 520                 525
Gln Ser Ala Leu Lys Lys Ile Phe Val Asp Gly Asp Ser Leu Phe Glu
        530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
            565                 570                 575
Phe Phe Ser Thr Asn Leu Val Glu Lys Ala Asn Thr Val Val Gly Ala
            580                 585                 590
Ser Leu Phe Val Asn Trp Val Lys Gly Val Ile Asp Asp Phe Thr Ser
        595                 600                 605
Glu Ser Thr Gln Lys Ser Thr Ile Asp Lys Val Ser Asp Val Ser Ile
        610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
            645                 650                 655
Met Glu Phe Ile Pro Glu Leu Ile Val Pro Ile Val Gly Phe Phe Thr
            660                 665                 670
Leu Glu Ser Tyr Val Gly Asn Lys Gly His Ile Ile Met Thr Ile Ser
        675                 680                 685
Asn Ala Leu Lys Lys Arg Asp Gln Lys Trp Thr Asp Met Tyr Gly Leu
        690                 695                 700
Ile Val Ser Gln Trp Leu Ser Thr Val Asn Thr Gln Phe Tyr Thr Ile
705                 710                 715                 720
Lys Glu Arg Met Tyr Asn Ala Leu Asn Asn Gln Ser Gln Ala Ile Glu
            725                 730                 735
Lys Ile Ile Glu Asp Gln Tyr Asn Arg Tyr Ser Glu Glu Asp Lys Met
            740                 745                 750
Asn Ile Asn Ile Asp Phe Asn Asp Ile Asp Phe Lys Leu Asn Gln Ser
        755                 760                 765
Ile Asn Leu Ala Ile Asn Asn Ile Asp Asp Phe Ile Asn Gln Cys Ser
        770                 775                 780
Ile Ser Tyr Leu Met Asn Arg Met Ile Pro Leu Ala Val Lys Lys Leu
785                 790                 795                 800
Lys Asp Phe Asp Asp Asn Leu Lys Arg Asp Leu Leu Glu Tyr Ile Asp
            805                 810                 815
```

Thr Asn Glu Leu Tyr Leu Leu Asp Glu Val Asn Ile Leu Lys Ser Lys
              820                 825                 830

Val Asn Arg His Leu Lys Asp Ser Ile Pro Phe Asp Leu Ser Leu Tyr
              835                 840                 845

Thr Lys Asp Thr Ile Leu Ile Gln Val Phe Asn Asn Tyr Ile Ser Asn
          850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
              885                 890                 895

Ile Phe Asn Asp Ile Gly Asn Gly Gln Phe Lys Leu Asn Asn Ser Glu
              900                 905                 910

Asn Ser Asn Ile Thr Ala His Gln Ser Lys Phe Val Val Tyr Asp Ser
              915                 920                 925

Met Phe Asp Asn Phe Ser Ile Asn Phe Trp Val Arg Thr Pro Lys Tyr
              930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
              965                 970                 975

Arg Ile Ile Trp Thr Leu Ile Asp Val Asn Ala Lys Ser Lys Ser Ile
              980                 985                 990

Phe Phe Glu Tyr Ser Ile Lys Asp Asn Ile Ser Asp Tyr Ile Asn Lys
              995                 1000                1005

Trp Phe Ser Ile Thr Ile Thr Asn Asp Arg Leu Gly Asn Ala Asn
              1010                1015                1020

Ile Tyr Ile Asn Gly Ser Leu Lys Lys Ser Glu Lys Ile Leu Asn
              1025                1030                1035

Leu Asp Arg Ile Asn Ser Ser Asn Asp Ile Asp Phe Lys Leu Ile
              1040                1045                1050

Asn Cys Thr Asp Thr Thr Lys Phe Val Trp Ile Lys Asp Phe Asn
              1055                1060                1065

Ile Phe Gly Arg Glu Leu Asn Ala Thr Glu Val Ser Ser Leu Tyr
              1070                1075                1080

Trp Ile Gln Ser Ser Thr Asn Thr Leu Lys Asp Phe Trp Gly Asn
              1085                1090                1095

Pro Leu Arg Tyr Asp Thr Gln Tyr Tyr Leu Phe Asn Gln Gly Met
              1100                1105                1110

Gln Asn Ile Tyr Ile Lys Tyr Phe Ser Lys Ala Ser Met Gly Glu
              1115                1120                1125

Thr Ala Pro Arg Thr Asn Phe Asn Asn Ala Ala Ile Asn Tyr Gln
              1130                1135                1140

Asn Leu Tyr Leu Gly Leu Arg Phe Ile Ile Lys Lys Ala Ser Asn
              1145                1150                1155

Ser Arg Asn Ile Asn Asn Asp Asn Ile Val Arg Glu Gly Asp Tyr
              1160                1165                1170

Ile Tyr Leu Asn Ile Asp Asn Ile Ser Asp Glu Ser Tyr Arg Val
              1175                1180                1185

Tyr Val Leu Val Asn Ser Lys Glu Ile Gln Thr Gln Leu Phe Leu
              1190                1195                1200

Ala Pro Ile Asn Asp Asp Pro Thr Phe Tyr Asp Val Leu Gln Ile
              1205                1210                1215

Lys Lys Tyr Tyr Glu Lys Thr Thr Tyr Asn Cys Gln Ile Leu Cys

```
                    1220                1225                1230

Glu Lys Asp Thr Lys Thr Phe Gly Leu Phe Gly Ile Gly Lys Phe
            1235                1240                1245

Val Lys Asp Tyr Gly Tyr Val Trp Asp Thr Tyr Asp Asn Tyr Phe
    1250                1255                1260

Cys Ile Ser Gln Trp Tyr Leu Arg Arg Ile Ser Glu Asn Ile Asn
        1265                1270                1275

Lys Leu Arg Leu Gly Cys Asn Trp Gln Phe Ile Pro Val Asp Glu
    1280                1285                1290

Gly Trp Thr Glu
        1295

<210> SEQ ID NO 24
<211> LENGTH: 1315
<212> TYPE: PRT
<213> ORGANISM: Clostridium tetani

<400> SEQUENCE: 24

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285
```

-continued

```
Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                    325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
        370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
                420                 425                 430

Ser Lys Leu Ile Gly Leu Cys Lys Lys Ile Pro Pro Thr Asn Ile
            435                 440                 445

Arg Glu Asn Leu Tyr Asn Arg Thr Ala Ser Leu Thr Asp Leu Gly Gly
        450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
                500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
        530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Asp Asp Phe Thr
610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
                660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
        690                 695                 700

Asp Asn Phe Leu Glu Lys Arg Tyr Glu Lys Trp Ile Glu Val Tyr Lys
```

-continued

```
            705                 710                 715                 720
Leu Val Lys Ala Lys Trp Leu Gly Thr Val Asn Thr Gln Phe Gln Lys
                    725                 730                 735
Arg Ser Tyr Gln Met Tyr Arg Ser Leu Glu Tyr Gln Val Asp Ala Ile
                    740                 745                 750
Lys Lys Ile Ile Asp Tyr Glu Tyr Lys Ile Tyr Ser Gly Pro Asp Lys
                    755                 760                 765
Glu Gln Ile Ala Asp Glu Ile Asn Asn Leu Lys Asn Lys Leu Glu Glu
                    770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
                    805                 810                 815
Leu Leu Glu Phe Asp Thr Gln Ser Lys Asn Ile Leu Met Gln Tyr Ile
                    820                 825                 830
Lys Ala Asn Ser Lys Phe Ile Gly Ile Thr Glu Leu Lys Lys Leu Glu
                    835                 840                 845
Ser Lys Ile Asn Lys Val Phe Ser Thr Pro Ile Pro Phe Ser Tyr Ser
850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
                    885                 890                 895
Ser Asp Ile Ser Gly Phe Asn Ser Ser Val Ile Thr Tyr Pro Asp Ala
                    900                 905                 910
Gln Leu Val Pro Gly Ile Asn Gly Lys Ala Ile His Leu Val Asn Asn
                    915                 920                 925
Glu Ser Ser Glu Val Ile Val His Lys Ala Met Asp Ile Glu Tyr Asn
                    930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
                    965                 970                 975
Ile Ser Ser Met Lys Lys His Ser Leu Ser Ile Gly Ser Gly Trp Ser
                    980                 985                 990
Val Ser Leu Lys Gly Asn Asn Leu Ile Trp Thr Leu Lys Asp Ser Ala
                    995                 1000                1005
Gly Glu Val Arg Gln Ile Thr Phe Arg Asp Leu Pro Asp Lys Phe
                    1010                1015                1020
Asn Ala Tyr Leu Ala Asn Lys Trp Val Phe Ile Thr Ile Thr Asn
                    1025                1030                1035
Asp Arg Leu Ser Ser Ala Asn Leu Tyr Ile Asn Gly Val Leu Met
                    1040                1045                1050
Gly Ser Ala Glu Ile Thr Gly Leu Gly Ala Ile Arg Glu Asp Asn
                    1055                1060                1065
Asn Ile Thr Leu Lys Leu Asp Arg Cys Asn Asn Asn Asn Gln Tyr
                    1070                1075                1080
Val Ser Ile Asp Lys Phe Arg Ile Phe Cys Lys Ala Leu Asn Pro
                    1085                1090                1095
Lys Glu Ile Glu Lys Leu Tyr Thr Ser Tyr Leu Ser Ile Thr Phe
                    1100                1105                1110
Leu Arg Asp Phe Trp Gly Asn Pro Leu Arg Tyr Asp Thr Glu Tyr
                    1115                1120                1125
```

-continued

```
Tyr Leu Ile Pro Val Ala Ser Ser Ser Lys Asp Val Gln Leu Lys
    1130            1135                1140

Asn Ile Thr Asp Tyr Met Tyr Leu Thr Asn Ala Pro Ser Tyr Thr
    1145            1150                1155

Asn Gly Lys Leu Asn Ile Tyr Tyr Arg Arg Leu Tyr Asn Gly Leu
    1160            1165                1170

Lys Phe Ile Ile Lys Arg Tyr Thr Pro Asn Asn Glu Ile Asp Ser
    1175            1180                1185

Phe Val Lys Ser Gly Asp Phe Ile Lys Leu Tyr Val Ser Tyr Asn
    1190            1195                1200

Asn Asn Glu His Ile Val Gly Tyr Pro Lys Asp Gly Asn Ala Phe
    1205            1210                1215

Asn Asn Leu Asp Arg Ile Leu Arg Val Gly Tyr Asn Ala Pro Gly
    1220            1225                1230

Ile Pro Leu Tyr Lys Lys Met Glu Ala Val Lys Leu Arg Asp Leu
    1235            1240                1245

Lys Thr Tyr Ser Val Gln Leu Lys Leu Tyr Asp Asp Lys Asn Ala
    1250            1255                1260

Ser Leu Gly Leu Val Gly Thr His Asn Gly Gln Ile Gly Asn Asp
    1265            1270                1275

Pro Asn Arg Asp Ile Leu Ile Ala Ser Asn Trp Tyr Phe Asn His
    1280            1285                1290

Leu Lys Asp Lys Ile Leu Gly Cys Asp Trp Tyr Phe Val Pro Thr
    1295            1300                1305

Asp Glu Gly Trp Thr Asn Asp
    1310            1315

<210> SEQ ID NO 25
<211> LENGTH: 11
<212> TYPE: PRT
<213> ORGANISM: Clostridium botulinum

<400> SEQUENCE: 25

Thr Lys Ser Leu Asp Lys Gly Tyr Asn Lys Ala
1               5                   10

<210> SEQ ID NO 26
<211> LENGTH: 7
<212> TYPE: PRT
<213> ORGANISM: artificial sequence
<220> FEATURE:
<223> OTHER INFORMATION: Tripeptide for affinity purification 1

<400> SEQUENCE: 26

Glu Leu Asp Lys Tyr Asn Cys
1               5

<210> SEQ ID NO 27
<211> LENGTH: 7
<212> TYPE: PRT
<213> ORGANISM: artificial sequence
<220> FEATURE:
<223> OTHER INFORMATION: Tripeptide for affinity purification 2

<400> SEQUENCE: 27

Asn Ile Ser Leu Asp Leu Cys
1               5

<210> SEQ ID NO 28
```

```
<211> LENGTH: 6
<212> TYPE: PRT
<213> ORGANISM: artificial sequence
<220> FEATURE:
<223> OTHER INFORMATION: Tripeptide for affinity purification 3

<400> SEQUENCE: 28

Tyr Tyr Asn Lys Phe Cys
1               5
```

MEANS AND METHODS FOR MANUFACTURING HIGHLY PURE NEUROTOXIN

The present invention relates to an antibody which specifically binds to unprocessed and/or partially processed neurotoxin polypeptide or an antibody which specifically binds an epitope consisting of a peptide having an amino acid sequence as shown in any one of SEQ ID NOs: 1 to 16. Moreover, the present invention relates to a method for manufacturing a Neurotoxin polypeptide, comprising the steps of, contacting a solution containing a mixture of proteolytically processed, partially processed and/or unprocessed neurotoxin polypeptides with an agent that specifically binds to unprocessed or partially processed Neurotoxin polypeptides but not to the processed neurotoxin polypeptides under conditions which allow binding of said agent to the unprocessed or partially processed neurotoxin polypeptides whereby an antigen-agent complex is formed, and removing the formed antigen-agent complex, whereby a solution containing processed neurotoxin polypeptide free of unprocessed or partially processed neurotoxin polypeptide is obtained. The present invention also relates to the use of the aforementioned antibody for separating proteolytically processed neurotoxin polypeptides from unprocessed or partially processed neurotoxin polypeptides. The present invention relates to a method for the manufacture of a medicament comprising the steps of the above method and the further step of formulating the proteolytically processed neurotoxin polypeptides as medicament. Furthermore, the present invention relates to a composition comprising the proteolytically processed neurotoxin polypeptide obtainable by the aforementioned method.

*Clostridium botulinum* and *Clostridium tetani* produce highly potent neurotoxins, i.e. botulinum toxins (BoNTs) and tetanus toxin (TeNT), respectively. These Clostridial neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by bacterial protease(s). Active dichain neurotoxin consists of two chains, an N-terminal light chain of approx. 50 kDa and a heavy chain of approx. 100 kDa linked by a disulfide bond. CNTs structurally consist of three domains, i.e. the catalytic light chain, the heavy chain encompassing the translocation domain (N-terminal half) and the receptor binding domain (C-terminal half), see Krieglstein 1990, Eur J Biochem 188, 39; Krieglstein 1991, *Eur J Biochem* 202, 41; Krieglstein 1994, J Protein Chem 13, 49.

*Clostridium botulinum* secretes seven antigenically distinct serotypes designated A to G of the botulinum neurotoxin (BoNT). All serotypes together with the related tetanus neurotoxin (TeNT) secreted by *Clostridium tetani*, are $Zn^{2+}$-endoproteases that block synaptic exocytosis by cleaving SNARE proteins. CNTs cause the flaccid muscular paralysis seen in botulism and tetanus, see Fischer 2007, PNAS 104, 10447.

Despite its toxic effects, botulinum toxin complex has been used as a therapeutic agent in a large number of diseases. Botulinum toxin serotype A was approved for human use in the United States in 1989 for the treatment of strabism, blepharospasm, and other disorders. It is commercially available as a Botulinum toxin A protein preparation, for example, under the tradename BOTOX (Allergan Inc) under the tradename DYSPORT (Ipsen Ltd). For therapeutic application the complex is injected directly into the muscle to be treated. At physiological pH, the toxin is released from the protein complex and the desired pharmacological effect takes place. An improved BoNT/A preparation being free of complexing proteins is available under the tradename XEOMIN (Merz Pharmaceuticals GmbH). The effect of Botulinum toxin is only temporary, which is the reason why repeated administration of Botulinum toxin may be required to maintain a therapeutic affect.

The Clostridial neurotoxins weaken voluntary muscle strength and are effective therapy of strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction, see Jost 2007, Drugs 67, 669.

For the manufacture of Clostridial neurotoxins, the purification of the neurotoxin containing fermentation solution is of particular importance. In this context, different precipitation- and extraction steps followed by a concentration step and further distinct chromatographic steps are usually applied in order to obtain purified neurotoxin, see DasGupta 1984, Toxicon 22, 415; Sathyamoorthy 1985, J Biol Chemistry 260, 10461. Currently, available neurotoxin preparations comprise, in addition to the desired active (processed) neurotoxin, a proteolytically unprocessed precursor and/or partially processed neurotoxin polypeptide. The proteolytically unprocessed precursor or partially processed polypeptide differs from the active (processed) neurotoxin polypeptide in a sequence of only a few amino acids. Therefore, they can hardly be distinguished based on their chemical and physical properties. On the other hand, the ratio of proteolytically unprocessed precursor and/or partially processed neurotoxin polypeptide of the total protein ratio is still significant in such preparations. Said ratio is due to the biological system, and is determined by the biosynthesis and the conditions of the fermentation process. Thus, the amount of undesired proteolytically unprocessed precursor and/or partially processed Neurotoxin polypeptide in Neurotoxin preparations is predefined and, currently, rather difficult to reduce.

Means and methods for reducing the amount of the unprocessed and/or partially processed neurotoxin polypeptides and thereby improving the quality of neurotoxin preparations are highly desirable but not yet available.

Thus, the technical problem underlying the present invention may be seen as the provision of means and methods for improving the manufacture of neurotoxin polypeptides by complying with the aforementioned needs. The technical problem is solved by the embodiments characterized in the claims and herein below.

The present invention relates to an antibody that specifically binds an epitope consisting of a peptide having an amino acid sequence as shown in any one of SEQ ID NOs: 1 to 16.

The term "antibody" as used herein encompasses a monoclonal antibody, a polyclonal antibody, a single chain antibody, a human, humanized, primatized, or chimerized antibody, a bispecific antibody, a synthetic antibody, chemically or enzymatically modified derivatives, a fragment of any of said antibodies or aptamers consisting of naturally occurring and/or chemically modified nucleic acids. Fragments of said antibodies include F(ab')$_2$, F(ab), Fv or scFv fragments or chemically or enzymatically modified derivatives of any of these fragments. The antibody of the present invention shall specifically bind to the epitope consisting of the aforementioned peptide if the said peptide is comprised by the partially processed or the unprocessed neurotoxin polypeptide.

The term "epitope" as in accordance with the present invention relates to the antigenic determinant which is recognized by the antibody of the present invention. It consists of a peptide having an amino acid sequence as shown in any one of SEQ ID NOs: 1 to 16. The aforementioned epitopes represent, in an aspect of the invention, peptides which are flanked by the cleavage sites for neurotoxin processing enzymes or which cover the cleavage site(s), see tables 1 and 2 below. The epitope is, in an aspect of the invention, comprised by a proteolytically unprocessed neurotoxin polypeptide or by a partially processed neurotoxin polypeptide. The partially processed neurotoxin polypeptide may either be the light chain of the neurotoxin polypeptide elongated with the peptide sequences as shown in any one of SEQ ID NOs: 1 to 8, or the heavy chain of the neurotoxin polypeptide elongated with the peptide sequences as shown in any one of SEQ ID NOs: 1 to 8. Due to the presence of said epitope, the unprocessed or partially processed neurotoxin polypeptides can be specifically bound by the antibody.

TABLE 1

Amino acid sequences of the epitopes and of the full length polypeptides of the Neurotoxin serotypes

| SEQ ID NO: | Sequence of the excised peptide | Cleavage sites | Neurotoxin/ Bacterial strain | SEQ ID NO: (full length Neurotoxin) | Accession-NO: |
|---|---|---|---|---|---|
| 1[b] | TKSLDKGYNK | K438/T439 K448/A449 | BoNT/A (Hall/62A) | 17 | ABD65472 |
| 2[c] | CKSVKAPGIC | K441/A442 | BoNT/B (Okra) | 18 | BAE48264 |
| 3[d] | SLYNK | R444/S445 K449/T450 | BoNT/C1 (C-6814) | 19 | BAA89713 |
| 4[d] | NSR | K442/N443 R445D446 | BoNT/D (CB16) | 20 | BAA90661 |
| 5[e] | GIR | K419/G420 R422/K423 | BoNT/E (Beluga) | 21 | CAA43999 |
| 6[d] | KGTK | R435/K436 K439/A440 | BoNT/F (NCTC10281) | 22 | CAA73972 |
| 7 | NGTK | nn | BoNT/G | 23 | CAA52275 |
| 8[a] | ENLYNR | R449 (z. T. R445) | TeNT | 24 | P04958 |

[a]Krieglstein et al. 1991, *Eur J Biochem* 202, 41-51.; Krieglstein et al. 1990, *Eur J Biochem* 188, 39-45.
[b]Beecher and DasGupta 1997, *J Protein Chem* 16, 701-712.; Krieglstein et al. 1994, *J Protein Chem* 13, 49-57.
[c]Antharavally and DasGupta 1998, *J Protein Chem* 17, 417-428.
[d]Sagane et al. 1999, *J Protein Chem* 18, 885-892.
[e]Antharavally and DasGupta 1997, *J Protein Chem* 16, 787-799.

TABLE 2

Amino acid sequences including the cleavage sites of the Neurotoxin serotypes

| SEQ ID NO: | Sequence including cleavage sites (highlighted) | Neurotoxin (Bacterial Strain) |
|---|---|---|
| 9 | KLLCVRGIITSKTKSLDKGYNKALN....DLCIKV | BoNT/A (Hall/62A) |
| 10 | IQMCKSVKAPG................ICIDV | BoNT/B (Okra) |
| 11 | TKFCHKAIDGRSL....YNKTL......DCRELLV | BoNT/C1 (C-6814) |
| 12 | TKVCLRLTK........NSRD......SDTCIKV | BoNT/D |
| 13 | IRFCKNIVSVKG......IRK........SICIEI | BoNT/E (Beluga) |
| 14 | VKFCKSVIPRKG......TKAP......PRLCIRV | BoNT/F (NCTC10281) |
| 15 | IAMCKPVMYKNT......GKS........EQCIIV | BoNT/G |
| 16 | IGLCKKIIPPTNIRENLYNRTASLTDLGGELCIKI | TeNT |

The term "specifically binds" means that the antibody of the present invention does not cross react to a significant extent with other epitopes either on said partially processed, or on said unprocessed neurotoxin polypeptides, or on other polypeptides in general. In an aspect of the invention, the antibody of the present invention does not cross react with said active, completely processed neurotoxin polypeptide. Epitope specificity is an important characteristic of the antibody of the present invention. Specificity of the antibody with respect to the partially processed or unprocessed neurotoxin versus the processed neurotoxin shall be, in an aspect, at least 95%, at least 96%, at least 97%, at least 98%, at least 99%. Specific binding can be tested by various well known techniques including, e.g., competition studies. Another important characteristic is the sensitivity of the antibody. Sensitivity shall be, in one aspect of the invention, such that at least 70%, at least 80%, at least 90%, at least 95% of the processed neurotoxin comprised by a sample is bound. Sensitivity can be tested by well known techniques. Those skilled in the art will be able to determine operative and optimal assay conditions for each determination by employing routine experimentation. Conventional techniques for binding studies include radioimmunoassay, ELISA, equilibrium dialysis, isothermal microcalorimetry, BIACORE® assays (surface plasmon reasonance, SPR) or other surface adsorption methods. The BIACORE® SPR system measures the antibody-antigen interaction. SPR response reflects a change in mass concentration at the detector surface as analytes bind or dissociate. Based on SPR, real-time BIACORE® measurements monitor interactions directly as they occur, see BIAapplications Handbook, version AB (reprinted 1998), BIACORE® code No: BR-1001-86; BIAtechnology Handbook, version AB (reprinted 1998), BIACORE® code No: BR-1001-84. The binding properties such as sensitivity of an antibody of the present invention may, in principle, be determined by binding studies using an immobilized antigen (the ligand) presented on a sensor surface. The antibody to be tested (the analyte) will be provided in the mobile phase, i.e. in a solution. In some cases, the antigen is attached indirectly to the surface through binding to another immobilized molecule which is referred as the capturing molecule. When the antibody is injected in a discrete pulse across the surface with the immobilized antigens, essentially three phases can be subdivided: (i) Association of antibody with the antigen during sample injection; (ii) Equilibrium or steady state during sample injection, where the rate of antibody binding is balanced by dissociation from the antibody-antigen complex; (iii) Dissociation of antibody from the surface during buffer flow. It will be understood that such an assay can alternatively performed with immobilized antibodies to be investigated and an antigen containing solution as the mobile phase. The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$). In an aspect of the invention, the antibody of the present invention has a KD of less than 0.5 µM, in an aspect, less than 0.05 µM and, in another aspect, less than 0.02 µM.

The antibody as referred to in the present invention can be manufactured by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth Enzymol 73, 3. Said techniques comprise the fusion of mouse myeloma cells to spleen cells derived from immunized mammals. Antibodies can be further improved by techniques well known in the art. For example, surface plasmon resonance as employed in the BIACORE® system can be used to increase the efficiency of phage antibodies which bind to the aforementioned epitope within proteolytically unprocessed neurotoxin polypeptide, see Schier 1996, Human Antibodies Hybridomas 7, 97; Malmborg 1995, J. Immunol. Methods 183, 7.

In an aspect of the invention, the antibody according to the antibody of the present invention is, in one aspect, produced by using an oligopeptide comprising the aforementioned epitope. Such an oligopeptide can be produced synthetically or by recombinant expression. Alternatively, the antibody of the invention can be produced by applying natural occurring unprocessed or partially processed neurotoxin polypeptide. In the latter case, it is to be understood that the resulting antibodies shall be further tested for specificity with respect to the unprocessed and/or partially processed neurotoxin polypeptide(s). In a further aspect of the invention, a monoclonal antibody of the invention is produced by using partially processed or unprocessed neurotoxin polypeptide which can be treated by a detergent in order to make the epitope immunologically available. However, it will be understood that in a case were the antibody shall be directed against a conformational epitope, no such detergent treatment shall be carried out. In a further aspect, immune-stimulation agents such as keyhole limpet hemocyanin (KLH) may be also applied in such process, especially when using a synthetic oligopeptide.

The antibody as referred to in the present invention can be used, for example, for affinity chromatography, immunoprecipitation, and immunolocalization of the partially processed and/or unprocessed neurotoxin polypeptide as well as for the monitoring of the presence of said polypeptide in samples or in recombinant organisms.

In an aspect of the invention, the partially processed and/or unprocessed neurotoxin polypeptide is from *Clostridium* spp. In another aspect of the invention, it is from *Clostridium botulinum* selected from the group of *Clostridium botulinum* ATCC 3502, *Clostridium botulinum* ATCC 3502—Hall strain. The primary structure of the said unprocessed neurotoxin polypeptide from *Clostridium botulinum* is disclosed in Krieglstein 1994, J Protein Chem 13, 49.

*Clostridium* spp. as referred to herein is the genus of Gram-positive, endospore-forming, obligate anaerobic bacteria which belong to the Firmicutes. Clostridial neurotoxins may be produced by phenotypic and genetic different clostridia belonging to the species *Clostridium botulinum, Clostridium butyricum, Clostridium barati*, and *Clostridium tetani*. *Clostridium botulinum* as used herein is specie of a rod shaped, Gram-positive, obligate anaerobic bacterium which produces, besides the neurotoxins, oval, subterminal endospores, and is commonly found in soil.

Moreover, in a further aspect of the antibody of the present invention, said antibody is bound to a polypeptide carrier. In an aspect of the antibody of the present invention, the said polypeptide carrier is selected from the group consisting of: a FC-binding protein, Protein A and Protein G and an antibody which specifically binds to the antibody of the present invention. This may be for example, in an aspect, an antibody which is species specific. Such antibody specifically binds to the FC portion or F(ab) of the antibody of the invention. In another aspect of the antibody of the present invention said polypeptide carrier is Protein A from *Staphylococcus aureus*. The said polypeptide carrier can be used, in an aspect of the invention, for isolating the antibody of the present invention.

Moreover, in a further aspect of the antibody of the present invention, said antibody is bound to a matrix. In an aspect, said matrix is a solid matrix.

The term "bound" as used herein, relates to any type of connection between the antibody and the matrix as long as the said connection does not interfere essentially with binding of the antibody to the partially processed and/or unprocessed neurotoxin polypeptide. Said connection may be made by interactions including indirect or direct, non-reversible or reversible, physical and chemical, electrostatic, and/or covalent bonds. In an aspect, the antibody is covalently linked, either directly or via a linker molecule, to the matrix.

The term "matrix" as used in accordance with the present invention refers to a three dimensional structure or spatial arrangement capable of binding an antigen or an antibody. Well-known matrices comprise polypeptides, glass, polystyrene, polypropylene, polyethylene, polyethylene glycol (PEG), dextran, nylon, amylases, natural and modified celluloses, polyacrylamides, gabbros, and magnetite. A solid matrix is, in an aspect of the invention, a polysaccharide matrix selected from the group consisting of: sepharose, sephadex; agarose, sephacell, micro-cellulose, and alginate-beads. In another aspect, said solid matrix can consist of glass-beads, and/or polypeptide matrices.

The antibody may be bound to the said matrix via a linker, including small molecule compounds, peptide linker molecules and beads. The matrix can have virtually any possible structural configuration or arrangement as long as the coupled antibody is capable of binding to its antigen. Thus, the matrix may be spherical, as in a bead, or cylindrical, as in the inside surface of a test tube, or the external surface of a rod. Alternatively, the surface may be irregular or flat such as a sheet, test strip, etc. In one aspect the said supports include polystyrene beads.

The aforementioned matrix, in an aspect of the invention, has at least one binding site for the antibody of the present invention. In a further aspect of the invention, said matrix has additional binding sites for further antibodies which recognize other epitopes. In an aspect, said epitopes are other epitopes which allow for specific binding of the partially processed and/or unprocessed neurotoxin polypeptide. Further antibodies immobilized on the matrix also encompass antibodies which recognize bacterial polypeptides other than the neurotoxin polypeptides. Such further antibodies comprised by the matrix may be used to remove further undesired polypeptides and, thus, for further purification purposes of a Neurotoxin preparation. However, it is to be understood that in a further aspect the processed neurotoxin shall not be specifically bound by the antibodies immobilized on the matrix.

The aforementioned antibody of the present invention is suitable for the manufacture of processed neurotoxin polypeptide because it specifically binds to the above characterized epitope thus enabling the binding of the partially processed or the unprocessed neurotoxin polypeptide and further separating it from the active processed neurotoxin polypeptide. An antibody which is capable of binding and removing the undesired partially processed and unprocessed neurotoxin polypeptide avoids, in an aspect of the invention, interaction with the active processed neurotoxin polypeptide which retains its biological activity. Thanks to the present invention, purification of neurotoxin is possible whereby the desired active polypeptide remains essentially unaffected in its activity. The skilled worker knows that "activity" is obtained only after proteolytic cleavage of the unprocessed precursor neurotoxin polypeptide, even though said unprocessed precursor can exert some biological functions. Accordingly, the "proteolytically processed neurotoxin polypeptide" in an aspect of the invention, is biologically active neurotoxin polypeptide. The term "biologically active" as used in the present invention relates to the capability of the neurotoxin polypeptide of subsequent receptor binding, internalization, translocation across the endosomal membrane into the cytosol, and/or endoproteolytic cleavage of one or more proteins involved in synaptic vesicle membrane fusion.

It is to be understood that the definitions and explanations of the terms made above apply mutatis mutandis for all aspects described in this specification in the following except as otherwise indicated.

In another aspect of the present invention, a method for the manufacture of an antibody which specifically binds to unprocessed and/or partially processed neurotoxin polypeptide is provided, said method comprising the steps of:

a) contacting a polyclonal antiserum from a non-human animal which has been immunized using a peptide immunogen comprising an amino acid sequence as shown in SEQ ID NO: 25
with a peptide having SEQ ID NO: 25
under conditions which allow for the formation of a complex comprising the aforementioned peptide and an antibody which specifically binds to unprocessed or partially processed neurotoxin polypeptide;

b) removing the complex formed in step c) from the antiserum; and c) releasing the antibody which specifically binds to unprocessed or partially processed neurotoxin polypeptide from the said complex.

The term "peptide immunogen" as used above refers to an oligopeptide having an amino acid sequence as shown in SEQ ID NO: 25 which is provided in a manner as to allow eliciting of an immune response in a non-human animal. In an aspect said immunogen further comprises KLH and in yet a further aspect, said KLH is linked via a cystein and, in an aspect a C-terminal cystein, to the peptide having SEQ ID NO: 25 via the linker N-[gamma-maleimidobutyryloxy] succinimide ester (GMBS). How to link KLH to a peptide by a linker molecule such as GMBS is well known in the art or described in the accompanying Examples below. In another aspect the non-human animal is a mammal, in an aspect a rat, mouse, rabbit, sheep or goat. Prior to carrying out the method of the invention, a non-human animal which shall be the source of the polyclonal antiserum will be immunized using the aforementioned peptide immunogen. How to immunize a non-human animal is well known in the art and described in the accompanying Examples, below. As a result of the said immunization, the non-human animal will produce polyclonal antibodies against the peptide immunogen.

A polyclonal antiserum can be obtained from the non-human animal by various techniques. In an aspect it is obtained from blood, serum or plasma by standard techniques well known in the art and described in the accompanying Examples, below. The term "polyclonal antiserum", thus, includes purified and partially purified sera from the said animal. Such a polyclonal antiserum is the starting material for the aforementioned method. In addition to the desired antibody (or antibodies) which specifically binds to unprocessed and/or partially processed neurotoxin polypeptide, the polyclonal antiserum may comprise additional antibodies which do not specifically binds to unprocessed and/or partially processed neurotoxin polypeptide. These antibodies are separated form the desired specific antibodies by contacting the polyclonal antiserum with a peptide also having an amino acid sequence as shown in SEQ ID NO: 25. In an aspect, said peptide is immobilized on a carrier as described in detail elsewhere herein. As a result of the said contacting, a complex of the peptide and the specific antibodies is formed which can subsequently be removed from the polyclonal serum. The specific antibodies than can be released from the removed complex. Suitable techniques for releasing antibodies from such a complex are described elsewhere herein.

In another aspect said method further comprises prior to step a) the steps of
i) contacting the said polyclonal antiserum from an non-human animal which has been immunized using a peptide immunogen comprising an amino acid sequence as shown in SEQ ID NO: 25
with the following capture peptides SLD, LDK, and YNK under conditions which allow for the formation of capture complexes comprising unspecific antibodies comprised by the polyclonal antiserum and the capture peptides; and
ii) removing the capture complexes from the polyclonal antiserum.

In the studies underlying the invention, a polyclonal serum was raised against unprocessed Botulinum neurotoxin type A (BoNT/A), using the linker peptide coupled to KLH as immunogen (anti-linker peptide scBoNT/A-serum) in goats. Even after affinity purification, the serum showed cross-reactivity towards processed BoNT/A in a Western blot. It was demonstrated that the cross-reactivity depended on the recognition of tripeptides (SLD, LDK and YNK), which occurred in the linker peptide, as well as, in the light and heavy chains of processed BoNT/A. A second batch of the goat immunoserum was purified via two-step affinity chromatography, removing the cross-reactive tripeptide-antibodies. The second anti-linker peptide scBoNT/A-serum displayed no cross-reactivity against processed BoNT/A in a western blot. The tripeptides can be applied, in an aspect, for affinity purification in form of the derivatives shown in any one of SEQ ID Nos. 26 to 28.

In an aspect of the method steps a) to c) are carried out by means of affinity chromatography.

Affinity chromatography as used in the present invention refers to a technique for separating molecules in a mobile phase based on their different affinities for a stationary phase used in the chromatography. In an aspect, the said technique refers to selective adsorption and subsequent recovery of a compound from an immobilized ligand. In another aspect, the said technique is designed for highly specific and efficient purification of proteins and related compounds using appropriate selective ligands on beaded and porous matrices for binding target compounds, which can then be recovered under mild conditions. The said technique is based on a highly specific interaction such as that between antigen and antibody, enzyme and substrate, or receptor and ligand. In another aspect said affinity chromatography is perform as column chromatography. Affinity chromatography as characterized in detail above is in one aspect, immunoabsorber chromatography and, hydrophobic interaction chromatography (HIC), reverse phase chromatography, and in another aspect, immunoaffinity chromatography applying the binding agent which is in even a further aspect, the antibody of the present invention. A stationary phase as referred to herein in an aspect consists of the aforementioned agent as a solid matrix. Said agent is in one aspect, bound to a polypeptide carrier coupled to a solid matrix, and in another aspect, bound to protein A coupled to a solid matrix.

In a further aspect of the aforementioned method steps i) and ii) are carried out by means of affinity chromatography.

The present invention also pertains to a method for identifying and antibody which specifically binds to unprocessed and/or partially processed neurotoxin polypeptide comprising the steps of:

a) determining whether the antibody binds to a peptide having an amino acid sequence as shown in SEQ ID NO: 25; and
b) determining whether the antibody binds to peptides having the following amino acid sequences SLD, LDK and YNK,
wherein an antibody which binds to a peptide having an amino acid sequence as shown in SEQ ID NO: 25 but not to peptides having the following amino acid sequences SLD, LDK and YNK is identified as an antibody which specifically binds to unprocessed and/or partially processed neurotoxin polypeptide.

The term "determining" as used in accordance with the method for identifying an antibody encompasses well established techniques for determining antibody binding to a given peptide such as immunoblotting techniques (Western- or Dot-blot technologies), affinity chromatography, plasma surface resonance techniques (BIACORE® Assays) and the like. It will be understood that in an aspect the aforementioned binding of the antibody to the peptide or peptides is specific binding (i.e. binding without cross reactivity).

In an aspect, the aforementioned method for identifying an antibody is carried out for monoclonal antibodies. In an aspect, the method is used to screen hybridoma cell lines and subsequently produce monoclonal antibodies which specifically bind to unprocessed and/or partially processed neurotoxin polypeptide. In another aspect, the method can be applied to screen for polyclonal antibodies, e.g., peptide antibodies, which specifically bind to unprocessed and/or partially processed neurotoxin polypeptide. In an aspect, the method may be applied for confirmation of the specificity of an antibody manufactured by a method of the present invention referred to elsewhere in this specification.

The present invention also pertains to an antibody obtainable by the aforementioned method. In aspect the antibody is a polyclonal antibody. In a further aspect said antibody is coupled to a solid support.

The antibody of the invention, in an aspect, allows for the detection of partially processed and/or unprocessed neurotoxin polypeptide with a high sensitivity and specificity, in an aspect with a limit of detection of 50 to 80 pg/ml, in an aspect 69 pg/ml.

In principle, the aforementioned antibody can be used for the removal of partially processed and/or unprocessed neurotoxin polypeptide from processed neurotoxin polypeptide or for detecting partially processed and/or unprocessed BoNT/A in a sample.

In addition, the present invention relates to a method for manufacturing neurotoxin polypeptide comprising the steps of:
a) contacting a solution containing a mixture of proteolytically processed, partially processed and/or unprocessed neurotoxin polypeptides with an agent that specifically binds to unprocessed or partially processed neurotoxin polypeptides but not to the processed neurotoxin polypeptides under conditions which allow binding of said agent to the unprocessed or partially processed neurotoxin polypeptides whereby an agent-complex is formed, and
b) removing the agent-complex formed in step a) whereby a solution containing processed neurotoxin polypeptide free of unprocessed or partially processed neurotoxin polypeptide is obtained.

The term "contacting" as used herein refers to bringing at least two different compounds in physical proximity as to allow physical and/or chemical interaction of said compounds. In accordance with the method of this invention, the said two different compounds are, in an aspect, the agent that specifically binds the partially processed or the unprocessed neurotoxin polypeptide which are comprised by the solution. Contacting as meant herein is carried out under conditions and for a time being sufficient to allow interaction of the agent and the partially processed or the unprocessed neurotoxin polypeptide. Said interaction shall result in binding of the partially processed or the unprocessed neurotoxin polypeptide to the agent whereby an antigen-agent complex is formed. As set forth elsewhere herein, said interaction comprises various kinds of binding such as indirect and direct, non-reversible and reversible measures. Suitable conditions which allow for specific interaction of the agent and the solution. This is well known to the skilled worker and said condition can depend on the agent and the solution to be applied in the method determined without further ado. Moreover, a time being sufficient to allow interaction can also be determined by the skilled worker without further ado. Conditions for antibodies as agents are disclosed in the accompanying examples, below.

A solution as used herein refers to any solvent system containing neurotoxin polypeptide and its partially processed and/or unprocessed neurotoxin polypeptides. The solvent system furthermore comprises a solvent. The solvents encompassed, in various aspects of the invention, are water, aqueous buffer systems, organic solvents, and ionic liquids. In one aspect of the invention, it is an aqueous solvent system. Moreover, the solvent system, in addition to the neurotoxin polypeptide and the solvent may comprise further molecules as well, including further bacterial polypeptides.

The term "agent" as used herein refers to a compound which is capable of specifically binding the partially processed or the unprocessed neurotoxin polypeptide. Suitable compounds comprise polypeptides, peptides, antibodies, and organic chemical molecules. In an aspect of the present invention, an agent is a polypeptide, peptide or an antibody as specified elsewhere herein. Said agent in a further aspect of the present invention, has at least one binding site for the partially processed or the unprocessed neurotoxin polypeptide. In another aspect of the invention, said agent has additional binding sites for further antibodies which are capable to specifically bind the agent. In even another aspect of the invention, the agent is the antibody of the present invention as specified above. Moreover, in a further aspect, the agent can comprise different antibodies of the invention. For example, it is conceivable that as an agent in the sense of the invention an antibody according to the invention which specifically binds to the partially processed neurotoxin polypeptide is used in combination with an antibody of the invention which specifically binds to the unprocessed neurotoxin polypeptide. Alternatively, an agent in the sense of the invention may comprise two or more different antibodies of the invention wherein each antibody specifically binds to a different epitope present in the partially processed and unprocessed neurotoxin polypeptide.

In an aspect of the method of the invention, the agent is immobilized to a matrix as set forth elsewhere herein. In a further aspect, the immobilization is achieved by covalent direct or indirect binding of the agent to the matrix.

The term "specific binding" as used herein refers to the binding of the agent to the partially processed and/or the unprocessed neurotoxin polypeptide without any cross reaction with other neurotoxins, host cell proteins, or more other peptides, polypeptides, or other compounds. Specific binding can be tested by various well known techniques. In this respect it is referred to the definitions made above in connection with the antibody of the invention which apply mutatis mutandis.

The term "agent-complex" as used in the present invention refers to the agent bound to the partially processed or to the unprocessed neurotoxin polypeptide. However, the complex could, in addition, comprise further molecules. In an aspect of the invention, the complex can comprise molecules which stabilize the complex or which facilitate purification, e.g. by allowing interaction of the complex with further molecules or which facilitate precipitation of the complex. Additional molecules comprised by the complex, in an aspect of the invention, encompass secondary antibodies which specifically bind to the agent or to the complex as such. Said secondary antibodies may then also be bound by further antibodies or interaction molecules such as polypeptide carriers indirectly or directly. It is to be understood that the complex can also comprise further bacterial polypeptides, or other molecules comprised by the solution.

The term "removing" the antigen-agent complex as used in the present invention refers to the separation of the complexed partially processed and of the complexed unprocessed neurotoxin polypeptide from the active, processed neurotoxin containing solution. In one aspect of the invention, said removing is carried out by means of affinity chromatography, e.g., by using immunobeads, or by immunoprecipitation.

As a consequence of the removal of the partially processed and of the unprocessed neurotoxin polypeptide, the method of the present invention, in an aspect, provides the active processed neurotoxin polypeptide in highly pure form. The term "highly pure form" as used herein refers, in one aspect, to the active processed neurotoxin polypeptide free of detectable amounts of its partially processed or its unprocessed neurotoxin polypeptide, and in another aspect, to active processed neurotoxin polypeptide free of detectable amounts of other impurities as well. In an aspect, the detectable amount of partially processed or unprocessed neurotoxin is less than 2.5%, less than 1% or, in another aspect, less than 0.1%. In a further aspect of the present invention, active processed neurotoxin type A polypeptide as referred to herein shows under reducing conditions a detectable single band at 100 kDa, and a detectable single band at 50 kDa, but no band at 150 kDa where the partially processed or the unprocessed neurotoxin type A polypeptides normally occur when analyzed, e.g., by SDS-PAGE. It is to be understood that other polypeptide impurities can be determined by SDS PAGE as well. It is further to be understood that other serotypes of active processed neurotoxins can be analyzed respectively.

The method of the present invention, wherein said neurotoxin polypeptide is selected from the group consisting of:
a) a neurotoxin polypeptide BoNT/A, BoNT/B, BoNT/C1, BoNT/D, BoNT/E, BoNT/F, BoNT/G or TeNT, and
b) a neurotoxin polypeptide having an amino acid sequence being at least 40% identical to the amino acid sequence of the neurotoxin polypeptide of a)

The term "neurotoxin" as used in the present invention refers to the antigenically different serotypes of Botulinum neurotoxins, i.e. BoNT/A, BoNT/B, BoNT/C1, BoNT/D, BoNT/E, BoNT/F, BoNT/G, and to Tetanus Neurotoxin (TeNT). In an aspect, said BoNT/A has an amino acid sequence as shown in SEQ ID NO: 17, BoNT/B has an amino acid sequence as shown in SEQ ID NO: 18, BoNT/C1 has an amino acid sequence as shown in SEQ ID NO: 19, BoNT/D has an amino acid sequence as shown in SEQ ID NO: 20, BoNT/E has an amino acid sequence as shown in SEQ ID NO: 21, BoNT/F has an amino acid sequence as shown in SEQ ID NO: 22, BoNT/G has an amino acid sequence as shown in SEQ ID NO: 23, and TeNT has an amino acid sequence as shown in SEQ ID NO: 24.

In a further aspect of the method of the present invention, said neurotoxin polypeptide is a variant of any one of the aforementioned neurotoxin polypeptides which has a sequence which comprises at least one amino acid substitution, addition and/or deletion with respect to any one of SEQ ID NOs 17 to 24. In another aspect said variant neurotoxin polypeptide has an amino acid sequence being at least 40% sequence identical to the amino acid sequence of BoNT/A (SEQ ID NO: 17), BoNT/B (SEQ ID NO: 18), BoNT/C1 (SEQ ID NO: 19), BoNT/D (SEQ ID NO: 20), BoNT/E (SEQ ID NO: 21), BoNT/F (SEQ ID NO: 22), BoNT/G (SEQ ID NO: 23), or TeNT (SEQ ID NO: 24). In another aspect of the invention, the neurotoxin polypeptide has an amino acid sequence being at least 70%, at least 75%, at least 80%, at least 85%, at least 90%, at least 95%, at least 98% or at least 99% sequence identical to the amino acid sequence of BoNT/A, BoNT/B, BoNT/C1, BoNT/D, BoNT/E, BoNT/F, BoNT/G or TeNT. The term "identical" as used herein refers to sequence identity characterized as determination of the identity of amino acid sequences wherein the sequences are aligned so that the highest order match is obtained, and which can be calculated using published techniques or methods codified in computer programs such as, for example, BLASTP, BLASTN, FASTA, Altschul 1990, J Mol Biol 215, 403. The percent identity values are in one aspect calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (1987, J Mol Evolution 25, 351; Higgins 1989 CABIOS 5, 151) or the programs Gap and BestFit (Needleman and Wunsch 1970, J Mol Biol 48; 443; Smith and Waterman 1981, Adv Appl Math 2, 482), which are part of the GCG software packet (Genetics Computer Group 1991, 575 Science Drive, Madison, Wis., USA 53711), are to be used. The sequence identity values recited above in percent (%) are to be determined, in one aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

It will be understood that the aforementioned variants shall, in an aspect of the invention, retain the biological properties of neurotoxins. Those of skill in the art will appreciate that full biological activity is attained only after proteolytic activation, even though it is conceivable that the unprocessed precursor can exert some biological functions or be partially active. "Biological properties" as used herein refers to (a) receptor binding, (b) internalization, (c) translocation across the endosomal membrane into the cytosol, and/or (d) endoproteolytic cleavage of proteins involved in synaptic vesicle membrane fusion. In vivo assays for assessing biological activity include the mouse LD50 assay and the ex vivo mouse hemidiaphragm assay as described by Pearce L B, Borodic G E, First E R, MacCallum RD (1994) (Measurement of botulinum toxin activity: evaluation of the lethality assay. Toxicol Appl Pharmacol 128: 69-77) and Dressler D, Lange M, Bigalke H (2005) (The mouse diaphragm assay for detection of antibodies against botulinum toxin type B. Mov Disord 20:1617-1619). The biological activity is commonly expressed in Mouse Units (MU). As used herein, 1 MU is the amount of neurotoxic component, which kills 50% of a specified mouse population after intraperitoneal injection, i.e. the mouse i.p. LD50 (Schantz & Kauter, 1978). In a further aspect, the variants can be neurotoxins having improved or altered biological properties, e.g., they may comprise cleavage sites which are improved for enzyme recognition or may be improved for receptor binding or any other property specified above. It is conceivable that the concept of the present invention relies on the presence of one, two or more cleavage sites between light and heavy chain of the neurotoxin polypeptide while the nature of the cleavage site(s) and the particular amino acid sequence between them does not matter as long as the agent is specific for the partially processed or unprocessed neurotoxin polypeptide. Accordingly, it is another aspect, to replace protease recognition sites and the linker peptide between heavy- and light chain of the neurotoxin polypeptide or flanking sequences surrounding the cleavage site (in case of a single cleavage site).

In another aspect, the neurotoxin polypeptide in accordance with the method of the invention may be a chimeric molecule. Such said chimeric molecule, in one aspect, may have single domains substituted. Accordingly, in another aspect, the portion of the neurotoxin heavy chain is replaced by a portion of an FC domain of an antibody.

In an aspect, the neurotoxin polypeptide produced according to the method of the present invention may be used for analytical tools including ELISA, antigens for ELISA, and control standards.

To achieve a neurotoxin preparation being free of other impurities as well, further steps of purification well known in the art can be added to the aforementioned method of the present invention and will be explained in the following.

As follows from the above in one aspect of the method of the present invention, said method is performed by means of affinity chromatography.

In another aspect of the invention, the specific immunoabsorber is prepared for the immunoaffinity chromatography as follows:

synthesis of the specific oligopeptide (represented by any one of the SEQ ID NOs: 1 to 16 or 25) of the unprocessed or the partially processed precursor polypeptide in particular, preparation of a synthetic oligopeptide;

conjugation of the peptide to a suitable carrier for immunization (including hemocyanin, BSA, lipopolysaccarides, and other) specifically, binding of the oligopeptide to a polypeptide carrier;

immunization of animals to produce poly- or monoclonal antibodies in particular, immunization of rabbits or goats to produce polyclonal, and immunization of mice to produce monoclonal antibodies (at least ten animals need to be immunized, in order to obtain an affine antibody;

hybridoma cell lines are generated to produce monoclonal antibodies;

purification of the antibodies by conventional and affinity chromatography (for the latter the oligopeptide will be bound to a carrier) specifically, the antibodies are purified using for example Protein A or G and/or via the oligopeptide bound to a carrier (the latter was used for immunization) or via peptide affinity chromatography for removing unspecific antibodies followed by affinity chromatography;

cleavage of the specific antibodies in Fab fragments in particular, the specific antibodies are treated with a protease such as Papain in order to obtain the respective Fab fragments;

the Fab fragments are characterized to their binding properties prior to further applications;

the antibodies will be coupled to a column matrix such as activated sepharose in particular, specific Fab fragments are coupled to an active linkage group of a carrier material;

the immuno-absorber (in a column) is washed and equilibrated using a suitable buffer system;

the unprocessed or the partially processed precursor neurotoxin polypeptide is specifically bound to the immunoabsorber whereas the active, processed neurotoxin polypeptide passes through the column unchanged (without being bound to) and will be collected;

In another aspect of the method of the invention, size exclusion chromatography is performed in addition. By size exclusion chromatography as used in the present invention, particles are separated based on their size, i.e. on their hydrodynamic volume. A mobile phase is either an aqueous solution used to transport the sample (gel filtration chromatography), or an organic solvent (gel permeation chromatography). A stationary phase is either a gel medium (polyacrylamide, dextran or agarose) and filter under low pressure, or a silica, or crosslinked polystyrene medium under a higher pressure. In even another aspect, said size exclusion chromatography is performed as column chromatography. In a further aspect of the method of the present invention, said size exclusion chromatography is performed using molecular sieves with distinct pore sizes such as activated carbon, silica gel, zeolite.

The method of the present invention, in another aspect, further comprises ion exchange chromatography.

Ion exchange chromatography as used in the present invention separates molecules based on differences between the overall charge of the proteins and related compounds. It is used for protein purification, for purification of oligonucleotides, peptides, or other charged molecules. Such molecules may be present in the solution to be applied to the method of the purification as contaminations. The protein or the related compound of interest, in the present case the Neurotoxin, must have a charge opposite to that of the functional group attached to the resin in order to bind. Because this interaction is ionic, binding must take place under low ionic conditions. Elution is achieved by increasing the ionic strength to break up the ionic interaction, or by changing the pH of the protein. In an aspect of the method of the invention, said exchange chromatography is performed as column chromatography.

In one aspect, exchange chromatography as used in accordance with the present invention is ion exchange chromatography.

The ion exchange chromatography as used in the present invention is in a further aspect performed by cation and/or anion chromatography. In anion exchange chromatography as used herein the surface charge of the solutes (proteins, peptides, nucleic acids, endotoxins) which bind will be net negative, thus to get binding of a specific protein one should be near or above the pI of that protein. Commonly used anion exchange resins are Q-resin (Q Sepharose), a Quaternary amine; and DEAE (DiEthylAminoEthane) resin. Generally, an ion exchange resin is an insoluble matrix of small beads having a charged surface, used as an artificial zeolite. Different types of resins can be distinguished based on their functional groups including strongly acidic resins (sulfonic acid groups, eg. sodium polystyrene sulfonate or polyAMPS), strongly basic resins, (quaternary amino groups, e.g. trimethylammonium groups, eg. polyAPTAC), weakly acidic resins (mostly, carboxylic acid groups), weakly basic resins (primary, secondary, and/or ternary amino groups, e.g., polyethylene amine). There are also specialised types of resins can be further distinguishes including chelating resins (iminodiacetic acid, thiourea).

In cation exchange chromatography as used herein, the surface charge of the solutes (proteins, peptides, nucleic acids, endotoxins) which bind will be net positive, thus to get binding of a specific protein one should be near or below the pI of that protein. Commonly used cation exchange resins are S-resin, sulfate derivatives; and CM resins, carboxylate derived ions.

In an aspect of the method of the present invention said ion exchange chromatography is carried out prior to and/or after affinity chromatography. In another aspect of the method of the invention, said ion exchange chromatography as used herein is carried out prior to the affinity chromatography of the present invention.

Due to this measure, the risk of potential cross-reactivity or unspecific binding during affinity chromatography can be further avoided and reduced.

The method of the present invention allows for the manufacture of active processed neurotoxin free of unprocessed or partially processed precursor polypeptide and thus, obtaining higher amounts of the active processed neurotoxin polypeptide.

The present invention refers, in principle, to the use of the antibody of the present invention for separating the active processed neurotoxin from its unprocessed or partially processed precursor polypeptide. In one aspect, the antibody of the present invention is used for the separation of the unprocessed or partially processed precursor neurotoxin polypeptide from the active processed neurotoxin polypeptide, in solution containing a mixture of said polypeptides, and, thus, obtaining active processed neurotoxin polypeptide free of an unprocessed or partially processed precursor neurotoxin polypeptide as described in detail elsewhere herein.

The present invention also relates to a method for the manufacture of a medicament comprising the steps of the aforementioned method and the further step of formulating the proteolytically processed neurotoxin polypeptide as medicament.

The term "medicament" as used herein refers, in one aspect, to a pharmaceutical composition containing the biologically active (proteolytically processed) neurotoxin polypeptide as pharmaceutical active compound, wherein the pharmaceutical composition may be used for human or non-human therapy of various diseases or disorders in a therapeutically effective dose.

A pharmaceutical composition as used herein comprises the biologically active (proteolytically processed) Neurotoxin polypeptide of the present invention, and in one aspect, one or more pharmaceutically acceptable carrier. The active Neurotoxin can be present in liquid or lyophilized form. In an aspect, said compound can be present together with glycerol, protein stabilizers (e.g., human serum albumin (HAS)) or non-protein stabilizers.

The pharmaceutical composition is, in one aspect, administered topically. Conventionally used drug administration is administered intra-muscular, subcutaneous (near glands). However, depending on the nature and the mode of action of a compound the pharmaceutical composition may be administered by other routes as well.

The compound, i.e. the biologically active (proteolytically processed) neurotoxin polypeptide is the active ingredient of the composition, and is in one aspect administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables.

The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like.

A therapeutically effective dose refers to an amount of the compound to be used in a pharmaceutical composition of the present invention which prevents, ameliorates or treats the symptoms accompanying a disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The pharmaceutical compositions and formulations referred to herein are administered at least once in order to treat or ameliorate or prevent a disease or condition recited in this specification. However, the said pharmaceutical compositions may be administered more than one time.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescribers or users instructions in order to anticipate dose adjustments depending on the considered recipient.

The medicament according to the present invention may in a further aspect of the invention comprise drugs in addition to the biologically active (proteolytically processed) neurotoxin polypeptide which are added to the pharmaceutical composition during its formulation. Finally, it is to be understood that the formulation of a pharmaceutical composition takes place under GMP standardized conditions or the like in order to ensure quality, pharmaceutical security, and effectiveness of the medicament.

The present invention, in general, contemplates a composition comprising proteolytically processed neurotoxin polypeptide obtainable by the method of the present invention.

The term "composition" refers to any composition formulated in solid, liquid, aerosol (or gaseous) form. Said composition comprises the compound of the invention optionally together with suitable auxiliary compounds such as diluents or carriers or further ingredients. In this context, it is distinguished for the present invention between auxiliary compounds, i.e. compounds which do not contribute to the effects elicited by the compound of the present invention upon application of the composition for its desired purpose, and further ingredients, i.e. compounds which contribute a further effect or modulate the effect of the compound of the present invention. Suitable diluents and/or carriers depend on the purpose for which the composition is to be used and the other ingredients. The person skilled in the art can determine such suitable diluents and/or carriers without further ado. Examples of suitable carriers and/or diluents are disclosed elsewhere herein.

In a further aspect of the invention, the aforementioned composition is a medicament as specified elsewhere in the description in more detail. In one aspect the said medicament can be used for prevention and/or treatment of at least one of the following diseases and disorders: voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, in a further aspect also Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitant mutational dysphonia, upper oesophageal sphincter dysfunction, vocal fold granuloma, stuttering Gilles de Ia Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, myelon tumors. For details and symptoms see, e.g., Jost 2007, Drugs 67(5), 669 or Dressier 2000 in Botulinum Toxin Therapy, Thieme Verlag, Stuttgart, N.Y.

In another aspect of the invention, the composition is a cosmetic composition which can be formulated as described for a pharmaceutical composition above. For a cosmetic composition, likewise, it is envisaged that the compound of the present invention is in an aspect used in substantially pure form. Cosmetic compositions are, in a further aspect, to be applied intramuscular. In an even further aspect of the invention, cosmetic compositions comprising the neurotoxin can be formulated as an anti-wrinkle solution.

All references cited in this specification are herewith incorporated by reference with respect to their entire disclosure content and the disclosure content specifically mentioned in this specification.

The Figures Show:

FIG. 1: Scheme of the conventional chromatographic purification of neurotoxin polypeptide.

Figure 2:
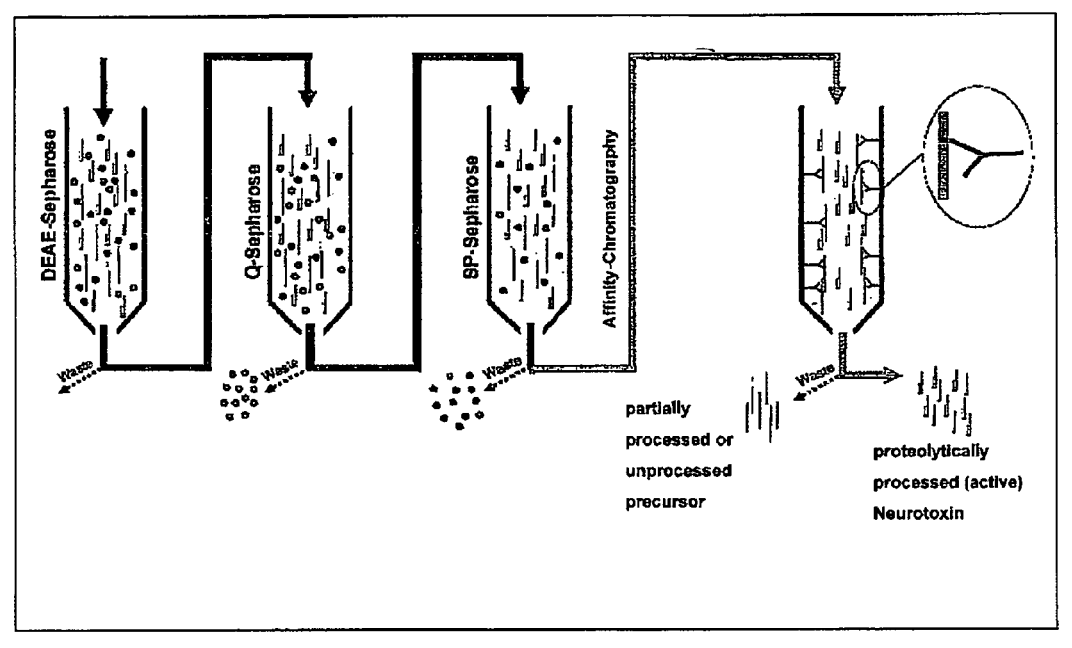

FIG. 2: Scheme of the chromatographic purification of biologically active (proteolytically processed) neurotoxin polypeptide and the separation of its partially processed or unprocessed polypeptide precursor according to the present invention.

FIG. 3: Western blot using an antibody which specifically recognizes SEQ ID NO: 25 and which has been obtained by the method of the present invention. Size of the bands is indicated in kDa. The individual lanes are explained in the Examples.

The following Examples illustrate the invention and shall, whatsoever, not be construed to limit its scope.

EXAMPLES

Example 1

Generation of Immunogen and Antibodies

Generation of Immunogens

1. Linkerpeptid-Immunogen I: The peptide with the sequence NH$_2$-TKSLDKGYNK-C-COOH was generated by an external provider and then coupled by the linker GMBS to the carrier-protein KLH.

2. Linkerpeptid-Immunogen II: a) Activation of ovalbumin; 2.18 mg sulfo-smcc (sulfosuccinimidyl-4(N-maleimidomethyl)cyclohexane-1-carboxylate) were solved in 50 μl DMSO. Subsequently, 2.5 ml ovalbumin solution containing 7.5 mg/ml ovalbumin (buffer: 5 mM sodiumphosphate; 0.9% NaCl) were added and the solution was incubated for 1 h at room temperature with rotation. A buffer change was performed using PD10 columns, activated ovalbumin was eluted in 3.5 ml buffer containing 10 mM sodiumphosphate; 0.9% NaCl. b) Coupling of the peptide to ovalbumin; 8 mg of the peptid Ac-DKGYNC-OH were solved in 250 μl H$_2$O and 2.5 μl 500 mM TCEP HCL (tris[2-carboxethyl]phosphine HCL) and subsequently neutralized with 1 mM NaoH. Finally, activated ovalbumin was added and the reaction mixture was incubated at room temperature for 4.4 h with rotation. By adding a 10 mM cysteine solution remaining reactive residues were blocked by incubation for 1 h with rotation. A dialysis was performed using 10 mM sodiumphosphate; 0.9% NaCl.

Immunization

Antisera were obtained by immunization.

1.) Anti-linkerpeptide scBoNT/A-serum I: As immunogen the linkerpeptide immunogen I was used which was coupled by the linker GMBS to the carrier-protein KLH. Two goats were immunized subcutaneously each first with 300 μg dekapeptid immunogen in Freud'schem adjuvant and finally immunized for four times in a 2 week rhythm with 100 μg immunogen in incomplete freud' schem adjuvant. After 49, 63, 77 and 84 days antisera were collected. Affinity chromatography was performed using the serum collected from the last bleeding on day 84.

2.) Anti-linkerpeptide scBoNT/A-serum II: As immunogen the linkerpeptide immunogen II was used which was coupled by the linker SMCC to the carrier-protein ovalbumin. Two rabbits were immunized intradermal each first with 300 μg linkerpeptide immunogen II in freud' schem adjuvant and finally immunized for five times in a 2 week rhythm with 150 μg linkerpeptide immunogen II in Montanide ISA 206. Affinity chromatography was performed using the serum collected from the bleeding on day 60 or 110, respectively.

Two Step Affinity Chromatography of the Sera

1. Generation of the matrix: For the two step affinity chromatography two different ultra link iodoacetyl matrices containing different peptides were generated.

On the one hand site the cross reactive peptides SLD, LDK and YNK were presented in form of the following peptides Ac-ELDKYN-C-COOH (SEQ ID NO: 26), NH$_2$-NISLDL-C-COOH (SEEQ ID NO: 27) and NH$_2$-YYNKF-C-COOH (SEQ ID NO: 28) and were coupled to the matrix using the general description given below. On the other hand the linker peptide (SEQ ID NO: 25) was coupled to the matrix using the general description given below in the form of the following derivative: Ac-TKSLDKGYNKA-C-COOH.

General Description:

Coupling Buffer: 50 mM Tris, 5 mM EDTA-Na, pH 8.5. Prepare a volume of buffer equal to 20 times the volume of UltraLink® Iodoacyl Gel to be used.

L-Cysteine HCL; Wash solution: 1 mM sodium chloride (NaCl).

Empty gravity-flow or spin column that may be capped both top and bottom:

Prepare the Peptide or Protein Sample

Dissolve the peptide with Coupling Buffer.

Couple to UltraLink® Iodoacyl Gel:

1. With the bottom cap in place on a gravity-flow column, add the desired quantity of the UltraLink® Iodoacyl Gel slurry, allow the gel to settle for 15 minutes.

2. Drain the liquid from the packed column and wash/equilibrate the UltraLink® Iodoacyl Gel with 5 gel-bed volumes of Coupling Buffer by adding buffer to the top of the gel bed allowing to drain through the column. Do not allow the gel bed to run dry.
3. Replace bottom cap and add the prepared sulfhydryl-containing sample. Approximately 1 ml of sample solution can be applied per ml of UltraLink® Iodoacyl Gel.
4. Replace the top cap and mix column at RT for 15 minutes.
5. Stand the column upright and incubate at RT for 30 minutes without mixing.
6. Sequentially remove top and bottom column caps and allow the solution to drain.
7. Wash column with three gel-bed volumes of Coupling Buffer.
Block Nonspecific Binding Sites on Gel.
1. Replace the bottom cap on column.
2. Prepare a solution of 50 mM L-Cysteine HCL in Coupling Buffer and add 1 ml of this solution to the column for each milliliter of gel.
3. Replace the top cap and mix for 15 minutes at RT, then incubate the reaction without mixing for an additional 30 minutes at RT.
2. Two step affinity chromatography:
Sera to be purified are first separated from blood.

The crude serum is given on the first column containing the cross reactive tripeptides. The cross reactive antibodies bind to the tripeptides and are separated from the crude serum. The filtrate of this first column is given to the second column containing the bound linkerpeptide. The linkerpeptide specific antibodies bind to the linkerpeptide. Low affinity anti-linkerpeptide scBoNT/A antibodies are removed from the column by a high stringency wash with PBS buffer (0.5 M NaCl). Subsequently, the bound high affinity anti linkerpeptide scBoNT/A antibodies are eluted and concentrated. This concentrate corresponds to the used anti linkerpeptide scBoNT/A serum.

Example 2

Test and Verification of Antibody Specificity

Reagents ELISA:
Coating buffer: 0.005 M-1M Tris; 0.9% NaCl, preferable 0.01 M-0.2 M Tris; 0.9% NaCl, pH=8.5.
Catcher antibody: anti linkerpeptide scBoNT/A serum.
Blocking and antibody diluent buffer: 0.5-5% BSA in 0.01 M sodium phosphate; 0.9% NaCl, pH=7.4.
Sample buffer: 0.5%-5% BSA in 0.005 M-1 M sodium phosphate; 0.1-0.5 M NaCl; 0.01%-1 Tween 20, preferably 1%-3% BSA in 0.005-0.1 M sodium phosphate; 0.15 M-0.4 M NaCl; 0.05%-0.5% Tween 20, pH=7.4.
Wash buffer: 0.01 M sodium phosphate; 0.9% NaCl; 0.05% Tween 20, pH=7.4.
Detection antibody: monoclonal antibody against BoNT/A.
Secondary antibody: A polyclonal anti mouse IgG (H&L) antibody conjugated to peroxidase.
Substrate: TMB, commercially available.
2. Reagents Western Blot:
Denaturating sample buffer, commercially available.
SDS gel, commercially available.
MES running buffer (SDS PAGE): commercially available.
PVDF membrane: commercially available.
Transfer buffer (Western Blot): commercially available.
Sample: Botulinum Neurotoxin A with Dichain-BoNT/A and scBoNT/A.
Primary antibody: anti linkerpeptid scBoNT/A serum.
Secondary antibody: polyclonal donkey anti goat antibody IgG (H&L) conjugated to alkaline phosphatase.
Blocking and antibody diluent buffer: 0.5%-5% BSA in 0.01 M-0.1 M Tris; 0.9% NaCl; 0.05-5% Tween 20, pH=7.4.
Washing buffer: 0.01 M-0.1 M Tris; 0.9% NaCl; 0.05-5 Tween 20, pH=7.4.
Tris buffer: 0.025 M Tris, pH=8.0.
Substrate: BCIP/NBT, commercially available.

a) Specificity of the antiserum with regard to BoNT/B and BoNT/E: For determining the specificity of the antisera with regard to BoNT/B and BoNT/E the recovery rate of substances were analyzed in ELISA. Microtiter plates are incubated with 100 µl/well of coating buffer containing 0.5 µg anti linkerpeptide scBoNT/A-serum/ml for 16 h at room temperature and subsequently washed three times with washing buffer. 200 µl/well blocking solution is added to the microtiter plates and incubated for 1 h at room temperature. The antigen scBoNT/A (dilution series in sample buffer; pg/ml concentration) is used as a calibration standard, microtiter plates are incubated with 100 µl/well calibration standard. BoNT/B or BoNT/E, respectively are diluted in sample buffer and applied to the microtiter plate in a volume of 100 µl/well. Both substances are applied in excess, a dilution of 200 ng/ml is used. Samples and standards are incubated for 2 h at 37° C. Microtiter plates are washed three times with washing buffer. 100 µl of detection buffer/well are added and incubated for 1 h at room temperature. Then microtiter plates are washed three times with washing buffer. Subsequently, the incubation with 100 µl/well of the secondary antibody for 1 h at room temperature is performed. Then microtiter plates are washed three times with washing buffer.

The detection reaction is started by adding 100 µl substrate/well. After incubation for 30 minutes at room temperature the reaction is stopped by adding 50 µl 2 M $H_2SO_4$/well and the absorbance is determined at 450 nm. For determination of specificity the concentrations of BoNT/b and BoNT/E are calculated by standardization. By calculating the recovery rate the specificity of the anti linkerpeptides scBoNT/A for sterotypes B and E can be determined. The lower the recovery rate, the lower the cross reactivity and the better the specificity of the serum in regard to scBoNT/A.

b) Specificity of the anti-linkerpeptide scBoNT/A with regard to Dichain BoNT/A: For determination of specificity of the antiserum in regard to activated Dichain-BoNT/A an immunohistological detection by Western blotting is performed. A NT sample (scBoNT/A at least 50 ng, Dichain-BoNT/A dependent on the sample used) is separated under reducing conditions by SDS-PAGE in accordance to their molecular weight into scBoNT/A, LC and HC (Dichain-BoNT/A). The proteins are then blotted onto a PVDF membrane. The membrane is blocked with 20 ml blocking buffer for 1 h at room temperature. The blocking buffer is removed and 20 ml of primary antibody solution containing 0.005 µg/ml anti linkerpeptide scBoNT/A serum are added. The primary antibody is incubated over night at 4° C. The antibody containing solution is removed and the membrane is washed three times for 30 minutes with 20 ml washing buffer at 37° C. Subsequently, the membrane is incubated for 3 h at room temperature with 20 ml of the secondary antibody in a concentration of 0.4 µg/ml. The secondary antibody solution is removed and the membrane is washed three times for 30 minutes with 20 ml washing buffer at 37° C. Additionally, the membrane is washed once with 20 ml of a 25 mM TRIS buffer for 5 minutes at room temperature.

The detection reaction is performed by adding the substrate. The substrate is incubated for 15 minutes and the color reaction is stopped by adding water. The specificity is determined by the staining of the scBoNT/A band at 150 kDa. Specificity of the anti linkerpeptide was determined when only the 150 kDa specific band was detected but no band specific for Dichain BoNT/A at 100 kDa (HC) and 50 kDa (LC). Fig: 3 shows in lane 3 the specificity for the 150 kDa scBoNT/A of a BoNT/A preparation (NT sample, see above). No bands are apparent at 100 kDa or 50 kDa, only the scBoNT/A is recognized. For comparison, in lane 4, a blend of partially processed and unprocessed scBoNT/A is shown and lane 5 shows a non-cleavable scBoNT/A control. Buffer control is shown in lane 2.

The invention claimed is:

1. A pharmaceutical composition comprising proteolytically processed, biologically active dichain neurotoxin, wherein the composition is free of detectable amounts of partially processed or unprocessed neurotoxin polypeptides, wherein the proteolytically processed, biologically active dichain neurotoxin is obtained by the steps of:
   a) contacting a solution comprising a mixture of processed and partially processed and/or unprocessed neurotoxin polypeptides with an antibody which has been raised against a peptide immunogen comprising the amino acid sequence of SEQ ID NO: 25;
   b) allowing the binding of the antibody to the unprocessed and/or partially processed neurotoxin polypeptides whereby complexes comprising the antibody and partially processed or unprocessed neurotoxin polypeptides are formed; and
   c) removing the complexes formed in step b) to obtain a solution of processed, active dichain neurotoxin, wherein the solution is free of detectable amounts of unprocessed and/or partially processed neurotoxin polypeptides; and
   d) formulating the solution of processed neurotoxin polypeptides obtained in step c) with at least one stabilizer of the biologically active dichain neurotoxin selected from protein stabilizers and non-protein stabilizers in pharmaceutically acceptable diluents, carriers, and/or adjuvants.

2. A method for obtaining a purified solution of processed neurotoxin polypeptides comprising the steps of:
   a) contacting a solution comprising a mixture of processed and partially processed and/or unprocessed neurotoxin polypeptides with an antibody which has been raised against a peptide immunogen comprising the amino acid sequence of SEQ ID NO: 25;
   b) allowing the binding of the antibody to the unprocessed and/or partially processed neurotoxin polypeptides whereby complexes comprising the antibody and partially processed and/or unprocessed neurotoxin polypeptides are formed;
   c) removing the complexes formed in step b) to obtain a solution of processed neurotoxin polypeptides which is flee of unprocessed and/or partially processed neurotoxin polypeptides; and
   d) formulating the solution of processed neurotoxin polypeptides obtained in step
   c) with at least one stabilizer of the biologically active dichain neurotoxin selected from protein stabilizers and non-protein stabilizers.

3. The method of claim 2, wherein steps a) to c) are carried out by affinity chromatography.

4. The method of claim 2, further comprising an on exchange chromatography step.

5. The method of claim 2, further comprising formulating the solution of processed neurotoxin polypeptides obtained in step d) in pharmaceutically acceptable diluents, carriers and/or adjuvants.

* * * * *

UNITED STATES PATENT AND TRADEMARK OFFICE
CERTIFICATE OF CORRECTION

PATENT NO. : 9,447,175 B2
APPLICATION NO. : 13/138452
DATED : September 20, 2016
INVENTOR(S) : Pfeil et al.

It is certified that error appears in the above-identified patent and that said Letters Patent is hereby corrected as shown below:

On the Title Page

Page 2, item (56), References Cited, Desler, Mov. Disorder: "1517" should be --1617--.

Page 2, item (56), References Cited, Ferreira J L, et al: "230" should be --203--.

In the Claims

Column 82, Line 25: "flee" should be --free--.

Column 82, Line 28: Remove hard return after the word "step".

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*